United States Patent [19]
McGlynn et al.

[11] Patent Number: 6,005,256
[45] Date of Patent: Dec. 21, 1999

[54] METHOD AND APPARATUS FOR PERFORMING CELL ANALYSIS BASED ON SIMULTANEOUS MULTIPLE MARKER EMISSIONS FROM NEOPLASIA (CASMMEN)

[75] Inventors: Charles L. McGlynn, Brookfield; Prasad R. Akkapeddi, Norwalk, both of Conn.

[73] Assignee: Raytheon Company, Lexington, Mass.

[21] Appl. No.: 09/022,641

[22] Filed: Feb. 12, 1998

[51] Int. Cl.$^6$ .................................................. G01N 21/86
[52] U.S. Cl. ..................................... 250/559.4; 250/461.2
[58] Field of Search ................................ 250/559.4, 221, 250/222.2, 461.1, 461.2; 356/346, 244, 246, 40, 39

[56] References Cited

U.S. PATENT DOCUMENTS 5,545,530  8/1996  Satomura et al. ........................ 435/6

*Primary Examiner*—Que T. Le
*Attorney, Agent, or Firm*—William C. Schubert; Glenn H. Lenzen, Jr.

[57] ABSTRACT

Disclosed are a method and apparatus for determining whether one or more organic substances, namely, proteins (42) and associated cancer cells (40'), are present in a sample (4a). The method comprises a step of deploying a plurality of fluorescent materials (40) in the tissue sample, individual ones of the plurality of fluorescent materials (40) being selected for coupling to a specific type of substance (42) of interest. The fluorescent materials (40) generally emit characteristic wavelengths in response to being illuminated with excitation light (14a'–14c') having predetermined excitation wavelengths. A next step includes illuminating the sample (4a) with the excitation light (14a'–14c'). The excitation light (14a'–14c') causes any of the fluorescent materials (40) that are disposed within the illuminated portion of the sample (4a), and which are responsive to the excitation wavelengths, to emit their characteristic wavelengths. Further steps include simultaneously detecting the presence of the emitted characteristic wavelengths, and, in response to detecting the presence of the emitted characteristic wavelengths, indicating that at least one of the substances (42) is present within the sample (4a). The invention enables the sample (4a) to be analyzed for the presence of multiple types of proteins (42) and associated cancer cells (40') simultaneously, using either a narrow band or broad band of excitation wavelengths. The invention also enables the proteins (42) and cancer cells (40') to be identified using a spectral and temporal analysis. These identifications are made regardless of whether or not the fluorescent materials (40) emit similar or different wavelengths.

15 Claims, 33 Drawing Sheets

| FIG.1a | FIG.1b |

| FIG.1c | FIG.1b |

| COLUMN 1 | COLUMN 2 | COLUMN 3 | COLUMN 4 | COLUMN 5 |
|---|---|---|---|---|
| MARKER | $\lambda$ EXCITATION (nm) | $\lambda$ EMISSION (nm) | $\Delta ex, cm$ | DECAY TIME CONSTANT (ns) |
| INDO 1 | 335 | 405/490 | 70 | |
| HOECHST | 346 | 460 | 114 | |
| AMCA | 347 | 445 | 98 | |
| DAPI | 359 | 461 | 102 | |
| GFP | 395 | 540 | 145 | |
| CASCADE BLUE | 399 | 423 | 24 | |
| LUCIFER YELLOW CH | 428 | 533 | 105 | |
| FURA RED | 436 | 640 | 204 | |
| BCECF | 439 | 530 | 91 | |
| CHROMOMYCIN | 458 | 590 | 132 | |
| PER CP | 470 | 680 | 210 | |
| R-PHYCOERYTHRIN | 480/565 | 578 | 98/13 | |
| DIO | 484 | 501 | 17 | |
| ACRIDINE ORANGE | 487 | 520/650 | 33/163 | |
| SNARF | 496 | 580/630 | 84/134 | |
| BCECF | 490 | 530 | 40 | |
| YOYO-I | 491 | 509 | 18 | |
| FITC | 494 | 520 | 26 | |
| FURA RED | 500 | 640 | 140 | |

FIG.3a

| MARKER | λ EXCITATION (nm) | λ EMISSION (nm) | Δex, cm | DECAY TIME CONSTANT (ns) |
|---|---|---|---|---|
| BIODIDY-FL | 503 | 533 | 30 | |
| RHODAMINE 123 | 505 | 512 | 7 | |
| FLUO-3 | 506 | 526 | 20 | |
| CALCIUM GREEN | 506 | 533 | 27 | |
| ETHIDIUM BROMIDE | 510 | | | |
| TOTO-1 | 514 | 533 | 19 | 1.7 |
| JC-1 | 514 | 529/590 | 15/76 | |
| PROPIDIUM IODIDE | 536 | 617 | 81 | |
| DIL | 547 | 565 | 18 | |
| CY3 | 550 | 565 | 15 | 1.8 |
| TRITC | 554 | 576 | 22 | |
| 7-AMINO ACT INOMYCIN D | 555 | 655 | 100 | |
| LISSAMINE RHODAMINE | 570 | 590 | 20 | 2.8 |
| BOBO-3 | 570 | 602 | 32 | |
| XRITC | 570 | 595 | 25 | |
| CALCIUM CRIMSON | 590 | 611 | 21 | |
| TEXAS RED | 596 | 615 | 19 | 4.2 |
| TOTO-3 | 642 | 660 | 18 | |
| CY5 | 650 | 670 | 20 | |
| ALLOPHYCOCYANIN | 650 | 661 | 11 | |

RANGE OF WAVELENGTH   335/650   405/680

FIG.3b

METHOD AND APPARATUS FOR PERFORMING CELL ANALYSIS BASED ON SIMULTANEOUS MULTIPLE MARKER EMISSIONS FROM NEOPLASIA (CASMMEN)

FIELD OF THE INVENTION

This invention relates generally to optical systems and methods and, in particular, to an imaging system which performs cancer analysis based on simultaneous multiple marker emissions from neoplasia.

BACKGROUND OF THE INVENTION

It is known that different types of neoplastic cells produce corresponding types of proteins. It is also known to examine a tissue sample to determine whether or not a particular type of protein is included in the sample, in order to make a further determination of whether or not the sample includes associated types of cancerous cells. By example, conventional techniques for performing this type of examination involve deploying a specific type of antibody and an associated fluorescent material (also referred to as a "marker") in the sample. Generally, assuming that there are cancerous cells and corresponding types of proteins included in the sample, the deployed antibody and marker become coupled to one or more of the proteins. Thereafter, using a conventional imaging system, the sample is illuminated using a specific wavelength that is known to "excite" the marker, causing the marker to fluoresce and emit fluorescent radiation of a particular wavelength. By detecting the wavelength of the emitted radiation using, for example, a radiation detector array component of the imaging system, a determination may then be made that the sample does in fact include proteins and associated cancerous cells. Otherwise, if there are no cancerous cells and corresponding proteins included in the sample, then the antibody and marker are generally not detectable using the "excitation" wavelength within the imaging system.

Unfortunately, conventional imaging systems for performing techniques such as the one described above suffer from a drawback of not being able to examine a sample for the presence of more than a single type of protein at a time, and only a single "excitation" wavelength is typically employed at a time rather than multiple excitation wavelengths. One reason for this is that conventional imaging systems typically do not include components for minimizing effects of undesired optical phenomena, such as optical scatter, which may occur in cases where multiple markers are excited using multiple excitation wavelengths. As a result, accurate determinations regarding whether or not marker emission wavelength detections indicate the presence of proteins in a sample generally cannot be made. Another shortcoming of conventional imaging systems is that these systems cannot distinguish between wavelengths emitted by different types of markers in cases where the emitted wavelengths are similar and are simultaneously emitted. For example, assuming that markers such as Lucifer Yellow CH and Calcium Green are employed in a sample being examined using a conventional imaging system, and that these markers are illuminated with wavelengths so as to cause the markers to simultaneously emit fluorescent radiation having similar wavelength values of 533 nm, the conventional imaging system cannot determine whether one or both of these markers actually fluoresced in response to being illuminated. As a result, accurate determinations regarding whether or not proteins are included in a sample cannot be made.

Being that conventional imaging systems cannot examine a tissue sample for the presence of more than a single type of protein at a time, in cases in which it is desired to determine whether or not more than one type of protein is included in a sample, it is necessary to add other individual types of markers to the sample for performing individual examinations for each type of protein being tested for. Alternatively, other tissue samples may need to be taken for the purpose of carrying out the above-described analysis for each type of protein. As can be appreciated, either one of these alternatives presents an undue burden to one who is analyzing the sample, especially in cases where it is necessary to examine the sample for the presence of many different types of cancer-related proteins.

In view of the foregoing description, it can be appreciated that it would be advantageous to provide an imaging system for performing cancer analysis of a tissue sample in a manner which overcomes the problems and shortcomings associated with prior art imaging systems.

OBJECTS OF THE INVENTION

It is an object of this invention to provide an improved imaging system for performing cancer analysis of a tissue sample.

It is another object of this invention to provide an imaging system which analyzes a tissue sample to determine whether or not the tissue sample includes cancer-related proteins, and which performs this analysis in a manner so that the sample is analyzed for the presence of multiple types of proteins simultaneously, using either a narrow band or broad band of excitation wavelengths.

It is another object of this invention to provide an imaging system which can identify whether or not cancer-related proteins are included in a tissue sample that includes fluorescent materials, based on an evaluation of fluorescent radiation wavelengths emitted by the fluorescent materials in response to being illuminated by one or more excitation wavelengths, wherein the identification can be made regardless of whether or not the fluorescent materials emit similar or different fluorescent radiation wavelengths.

Further objects and advantages of this invention will become apparent from a consideration of the drawings and ensuing description.

SUMMARY OF THE INVENTION

The foregoing and other problems are overcome and the objects of the invention are realized by a method and apparatus in accordance with this invention for determining whether one or more cancer-related proteins are present in a tissue sample. The method comprises a step of deploying multiple types of fluorescent materials in the tissue sample. The multiple types of fluorescent materials couple to corresponding types of the proteins, assuming that these proteins are included in the sample. A next step includes illuminating the tissue sample with at least one excitation wavelength to cause at least some of the fluorescent materials to emit their respective characteristic emission wavelengths. A next step includes simultaneously detecting the respective characteristic emission wavelengths emitted by these fluorescent materials, and then converting the respective characteristic emission wavelengths to respective signals. The signals correspond to the respective characteristic emission wavelengths emitted by the fluorescent materials. Next, a step is performed of detecting amplitudes of the signals and generating corresponding amplitude profiles. Further steps include determining that at least one of the detected amplitudes exceeds a predetermined threshold level, and in response to determining that at least one of the detected amplitudes exceeds the predetermined threshold level, indicating that at least one of the cancer-related proteins is present within the tissue sample.

In accordance with another aspect of the invention, the specific types of proteins included in the sample are identified using a spectral and temporal analysis of the invention. The analysis enables a simultaneous identification to be made of multiple types of proteins included in the sample. The temporal analysis enables marker fluorescent emission response "lifetimes" to be recorded, and enables any spectrally overlapping detected fluorescent responses to be evaluated and differentiated.

BRIEF DESCRIPTION OF THE DRAWINGS

The above set forth and other features of the invention are made more apparent in the ensuing Detailed Description of the Invention when read in conjunction with the attached Drawings, wherein:

FIGS. 3a and 3b show a table that identifies various exemplary types of fluorescent materials that may be employed in the sample 4a of FIG. 2a, and which further identifies corresponding "excitation" wavelengths, emission wavelengths, and decay time constants for these fluorescent materials;

FIG. 12 is a block diagram showing an exemplary system 60 within which the imaging system of the invention (labelled "56") may be employed to enable various types of medical data to be obtained regarding the sample 4a of FIG. 2a;

Identically labeled elements appearing in different ones of the figures refer to the same elements but may not be referenced in the description for all figures.

DETAILED DESCRIPTION OF THE INVENTION

Figure 2A:
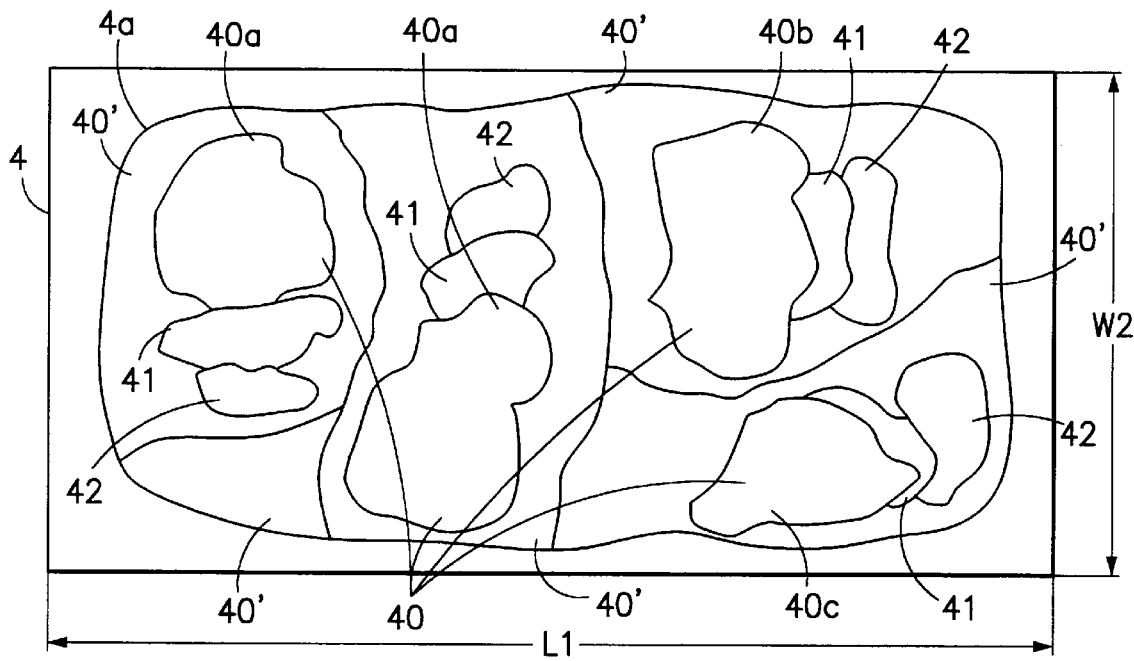
FIG. 2a shows an exemplary sample slide 4 having a sample 4a disposed thereon.

An exemplary representation of a substrate 4 is shown in FIG. 2a. As such, the substrate will hereinafter be referred to as "slide 4". The slide 4 is assumed to include a sample 4a comprised of tissue cells 40' (e.g., human tissue cells), which may be neoplasia (i.e., tumor) cells. It is assumed for the purposes of this invention that it is desired to examine the sample 4a to ascertain whether or not any of the cells 40' are cancerous, and also to identify the particular types of cancer cells, if any, that are present in the sample 4a. In accordance with this invention, a method and apparatus are provided that enable the sample 4a to be examined for the presence of various types of cancerous cells and cancer-related proteins simultaneously, and which also enables the proteins to be identified. The examination is accomplished by first placing in the sample 4a particular types of fluorescent materials (i.e., so called "markers") 40 and associated antibodies 41. More particularly, assuming that it is desired to examine the sample 4a for the presence of one or more particular types of cancerous cells, such as, for example, cells related to various, known types of breast cancer, then particular types of markers 40 and associated antibodies 41 that are known to bind themselves to proteins 42 associated with these cells are placed in the sample 4a. An example of various types of markers 40 that may be employed in the sample 4a is shown in a first column of the table of FIGS. 3a and 3b, although it should be noted that other types of fluorescent materials may also be employed, depending on the types of cancerous cells for which the sample 4a is being tested.

Upon placing the markers 40 and associated antibodies 41 in the sample 4a, and assuming that one or more of the cells 40' is indeed cancerous, then the markers 40 and antibodies 41 bind themselves to the proteins 42 associated with the cells 40'. Otherwise, assuming that the cells 40' included in the sample 4a are not cancerous cells, and that, as a result, do not produce the associated proteins 42, then the markers 40 and antibodies 41 placed in the sample 4a do not become coupled to the cells, and the markers 40 flush from the sample 4a and remain undetectable. It should be noted that typically a sufficient quantity of markers are deployed in the sample 4a so that, assuming there are one or more cancerous cells 40' and associated proteins 42 included in the sample 4a, the deployed markers 40 "cover" an area of the cancer cells 40' visible to the imaging system 1. After the markers 40 are added to the sample 4a, the sample 4a may be examined for the presence of multiple types of cancer-related proteins using an imaging system that is constructed and operated in accordance with this invention. The system, which will hereinafter be referred to as an "imaging system", performs the examination in accordance with a novel technique of the invention, enabling the sample 4a to be examined for the presence of more than a single type of cancer-related protein at a time, and, assuming that the sample 4a includes cancerous cells, enabling the cancer-related proteins to be identified, as will be further described below. The imaging system is a con-focal system.

Figures 1A, 1D:
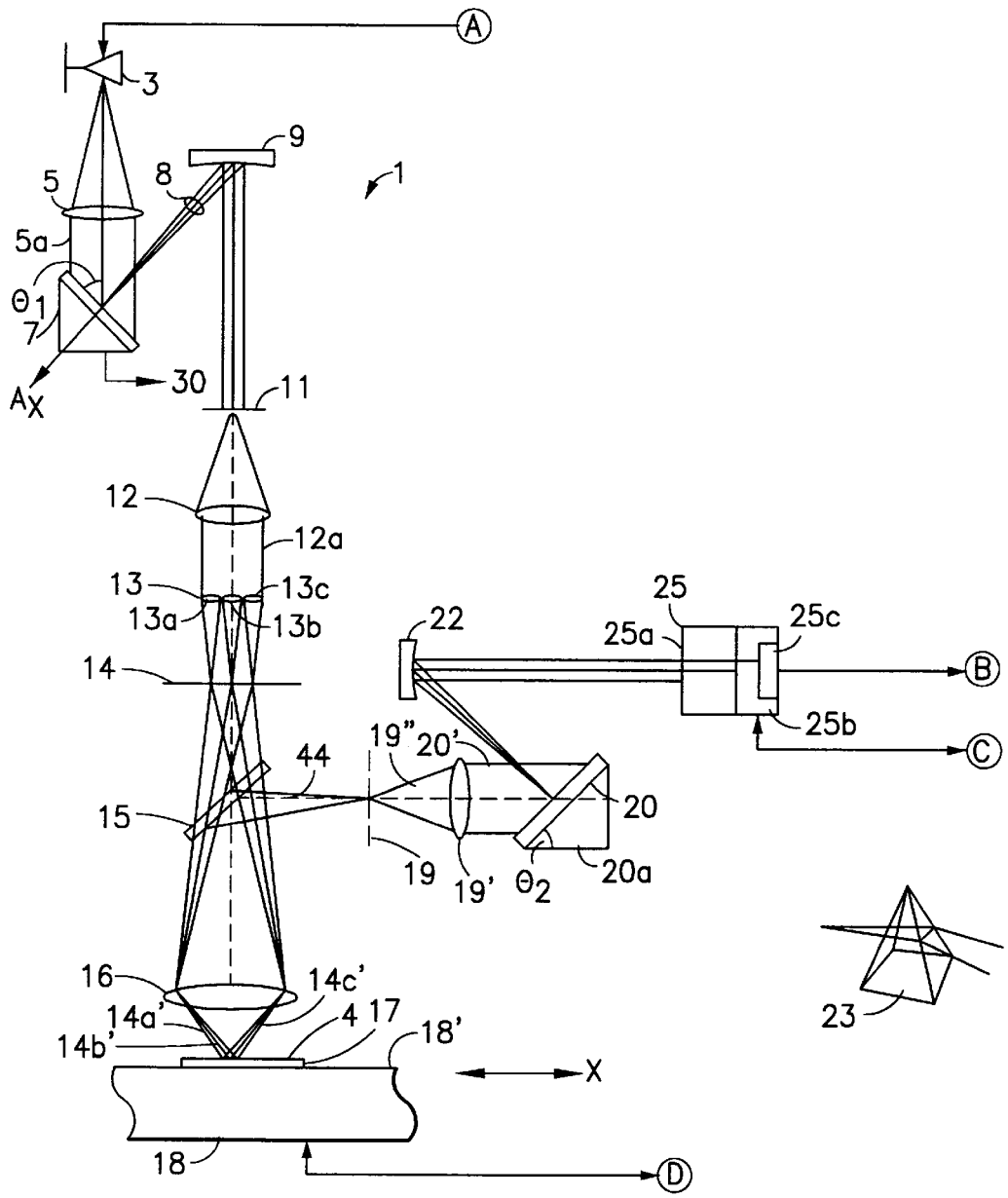
FIGS. 1a and 1b show an imaging system that is constructed in accordance with one embodiment of the invention.
FIG. 1d shows the manner in which FIGS. 1a and 1b relate to one another.
Figure 1B:
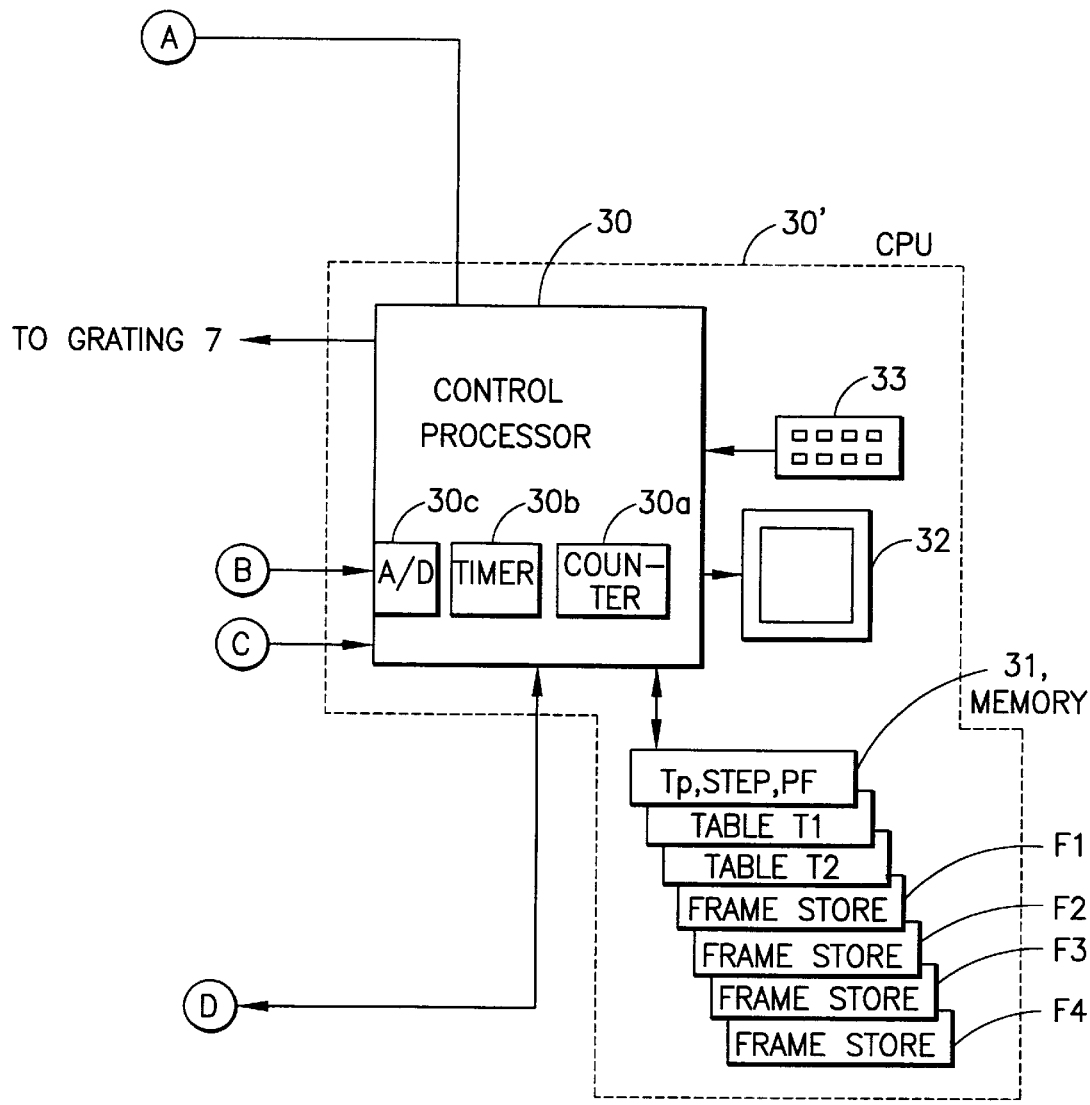

FIGS. 1a and 1b show a block diagram of the imaging system (labelled "1"), as constructed in accordance with one embodiment of this invention. The system 1 comprises a pulsed source illuminator 3, such as a pulsed laser or lamp, which is controllable by a control processor 30 of a CPU 30' for providing a pulsed beam to a collimating lens 5. In accordance with one embodiment of the invention, the source illuminator 3 is capable of providing a broad band of wavelengths, preferably within the range of 335 nm to 700 nm. The pulse rate of the source illuminator 3 may be varied under the control of the control processor 30. An operator of the CPU 30' may vary the pulse rate of the source illuminator 3 from the CPU 30' by entering appropriate information into the control processor 30 via a keypad 33. The pulse beam (also referred to as an "excitation pulse beam") preferably has a duration of at least ins, as will be further described below.

In response to receiving the pulsed beam from the source illuminator 3, the collimating lens 5 collimates the beam and provides a resultant, collimated pulse beam 5a to a grating 7. The grating 7 is rotatable about an axis $A_x$, under the control of the control processor 30, and is inclined so that there is an angle (θ1) between a plane in which the beam 5a extends and a plane in which an upper surface of the grating 7 extends, as can be appreciated in view of FIG. 1a. Depending on the value of angle (θ1), the grating 7 diffracts the received beam 5a to provide a resultant beam portion 8, which includes a particular narrowband of wavelengths, to a focusing optic 9. The focusing optic 9 preferably has a shape for collimating a received beam. In response to receiving the beam portion 8, the focusing optic 9 collimates the beam portion 8 into a corresponding collimated narrowband of wavelengths, and reflects these wavelengths to a monochrometer slit 11. Depending on the value of the angle (θ1) and on the particular angle of rotation of the grating 7, the monochrometer slit 11 transmits a particular one of the wavelengths (i.e., a desired wavelength, also referred to as an "excitation image") to a cylindrical lens 12.

As can be appreciated in view of FIG. 1a and the foregoing description, the combination of the components 5, 7, 9, and 11 functions to enable a desired wavelength to be transmitted from the slit 11 to the cylindrical lens 12. Preferably, this wavelength is one which is known to "excite" one or more of the types of markers 40 employed in the sample 4a, causing the marker(s) to emit corresponding fluorescent radiation.

It should be noted that the invention is not intended to be limited to this configuration for providing the desired wavelength through slit 11, and that in other embodiments of the invention, other, suitable components may be employed to provide the desired wavelength. By example, rather than components 5, 7, and 9, a single laser may be employed for providing a monochromatic beam of a desired wavelength directly to the slit 11, for enabling the desired wavelength to be provided to the cylindrical lens 12. Also by example, and referring to FIG. 1c which shows a portion of an imaging system 1' constructed in accordance with another embodiment of the invention, the grating 7 may be replaced with a mirror 7a so that more than a single one of the broad band wavelengths output by the source illuminator 3 are transmitted by the slit 11 to the cylindrical lens 12. This embodiment of the imaging system includes similar components as the imaging system 1 of FIGS. 1a and 1b, except that the grating 7 is replaced with the mirror 7a. Either of the embodiments of the imaging system (i.e., imaging system 1 or 1') of the invention may be employed to enable the sample 4a to be examined for the presence of various types of cancerous cells simultaneously, as will be described below.

In response to receiving one or more wavelengths from the slit 11, the cylindrical lens 12 provides a stripe beam 12a to a cylindrical lenslet array 13 located at a pupil of the system 1. The stripe beam 12a uniformly illuminates a volume of individual lenslets 13a–13c of the array 13.

Figure 6:
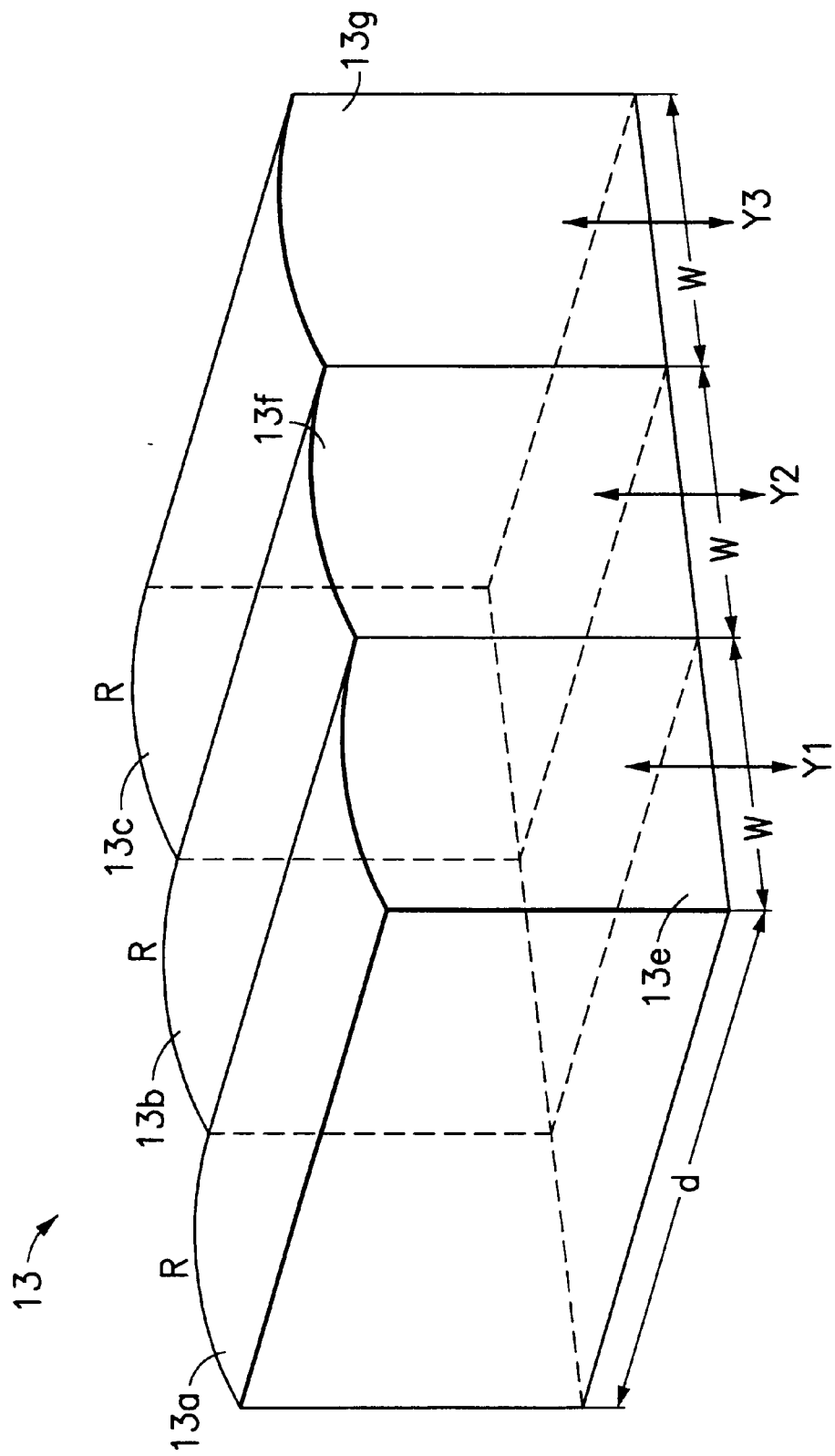
FIG. 6 shows a lenslet array 13 of the imaging system of FIGS. 1a and 1b.

A cross section of the lenslet array 13 is shown in FIG. 6. In a preferred embodiment of the invention, the lenslet array 13 includes three individual lenslets 13a–13c. Each individual lenslet 13a–13c of the array 13 has a depth (d) (e.g., where (d) preferably equals 6 mm) and a width (w) (e.g., where (w) preferably equals 1.26 mm), and preferably comprises fused silica. Also, an axis Y1, that is centered on a front face 13e of lenslet 13a, is preferably separated from an axis Y2 centered on a front face 13f of lenslet 13f by a distance of, e.g., 1.26 mm. Similarly, the axis Y2 is preferably separated from an axis Y3, which is centered on a front face 13g of lenslet 13c, by a distance of, for example, 1.26 mm. Each individual lenslet 13a–13c preferably has a radius of curvature that is substantially equal to the product of 2×f, where f represents the focal length of the lenslet. By example, each individual lenslet 13a–13c has a radius of curvature of approximately 9.5 mm. The lenslet 13a enables spatial separation to be provided between rows of images that are employed to illuminate the sample 4a, and thus enables unwanted optical background "noise" to be suppressed, as will be described below.

In response to being illuminated by the stripe beam 12a, each of the lenslets 13a–13c focuses a respective, received portion of the beam 12a to a respective portion of a mask 14, so as to cause a respective row of slits of the mask 14 to become uniformly illuminated. The beam portions focussed by the lenslets 13a–13c to the mask 14 are also collectively referred to as an "interrupted stripe beam", and provide multiple excitation images to the mask 14.

Figure 7:
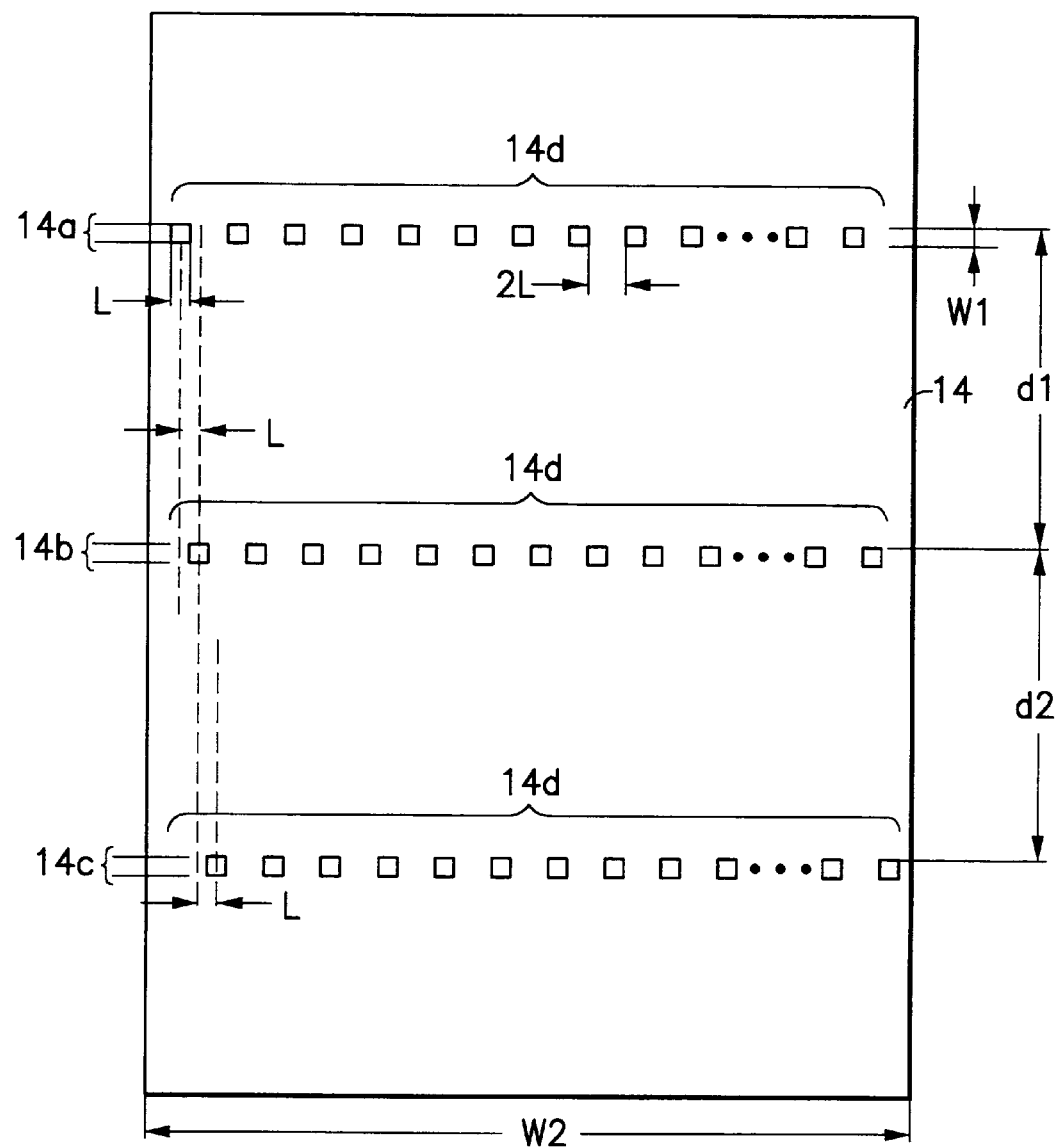
FIG. 7 shows a mask 14 of the portions of the imaging systems of FIGS. 1a and 1c, as viewed from a perspective looking down on the mask 14.

FIG. 7 shows the mask 14 in greater detail, as viewed from a perspective looking down on the mask 14. In accordance with a preferred embodiment of the invention, the mask 14 includes three rows of slits, namely rows 14a, 14b, and 14c. Each row 14a, 14b, and 14c preferably includes 85 individual slits (collectively as "14d") which are staggered with respect to slits of an adjacent one of the rows 14a–14c, as will be described below. Each individual slit has a length (L) and a width (W1). The slits 14d within each individual row 14a–14c are preferably spaced apart by a distance equivalent to 2 (L), and center lines of corresponding slits 14d of adjacent ones of the rows 14a–14c are preferably horizontally offset (i.e., staggered) from one another by a distance equivalent to length (L), as may be understood in view of FIG. 7. Moreover, the rows 14a–14c are spaced apart from one another so that there is a distance (d1) separating corresponding edges of slits of adjacent ones of the rows 14a–14c. Preferably, the distance (d1) is substantially equal to the product of 85×width (W1). Moreover, the mask 14 has a width (W2).

In accordance with the invention, because the individual slits 14d within each row 14a–14c are separated from one another by a distance equivalent to 2 (L), where (L) represents the length of an individual slit of the mask 14, the effects of undesired optical phenomena, such as optical scatter (which may result from marker autofluorescence), on the overall performance of the imaging system 1, are substantially minimized.

Referring again to FIG. 1a, upon being illuminated by the respective beams received from the lenslet array 13, the slits 14d of the respective rows 14a–14c of mask 14 transmit these beams to an objective 16, which, in turn, focuses these beams to an upper surface 18'0 of a stage 18 or, assuming that the sample slide 4 is disposed on the upper surface 18' of stage 18, to an upper surface of the sample slide 4.

The beams that are focused by the objective 16 onto the surface 18' of the stage 18 or onto the upper surface of the sample slide 4 are hereinafter referred to as "slit image beams", and images appearing on these components as a result of the slit image beams are hereinafter referred to as "slit images". Each of the slit images and associated slit image beams corresponds to a respective slit of a respective one of the rows 14a–14c. The slit image beams produced by the slits 14d of the respective individual slit rows 14a, 14b, and 14c, are hereinafter collectively referred to as slit image beam groups 14a', 14b', and 14c', respectively, and the slit images which correspond to these slit image beam groups 14a', 14b', and 14c' (and which appear on, and illuminate, the upper surface of the slide 4 or stage 18), are hereinafter referred to as slit image groups 14a", 14b", and 14c", respectively. In accordance with one embodiment of the invention, the objective 16 provides a 1:1 magnification level. By example, depending on the magnification level provided by the objective 16, each individual slit image may have a width (W') of 0.5 um, 2 um, 5 um, 20 um, or 50 um, and a distance (W") between an outer edge of a first slit image of each group 14a"–14c" and an outer edge of a last one of the slit images of the group 14a"–14c" may be 0.13 mm, 0.64 mm, 5.12 mm, 12.8 mm (see, e.g., FIG. 10a).

The stage 18 may be any suitable type of stage device known in the art that is controllable for displacing objects, such as sample slide 4, along one or more axes of the (x,y,z) coordinate system. The stage 18 operates under the control processor 30 for displacing the slide 4 along desired ones of the axes (x, y, z). Preferably, the stage 18 can displace the sample slide 4 along desired ones of these axes (x, y, z) by distances that are at least as small as the width (W1) of individual ones of the slits 14d of the mask 14. By example, and in accordance with one embodiment of the invention, the stage 18 has a capability of displacing the sample slide 4 along desired ones of the axes (x, y, z) by distances that are at least as small as 6/10 microns.

A further portion of the imaging system 1 of the invention will now be described. For the purposes of describing this portion of the imaging system 1, it is assumed that the sample slide 4 is disposed over the top surface 18' of the stage 18 in a position so that, after a pulse beam is fired from source illuminator 3, at least some portion of the sample 4a becomes illuminated by one or more of the slit image groups 14a"–14c". It is also assumed that one or more of the cells 40' of the sample 4a are cancerous, that the sample 4a includes a plurality of markers 40, and that at least some of these markers become illuminated by one or more of the slit images from at least one of the slit image groups 14a"–14c". Depending on the wavelength(s) of the pulse beam fired by the source illuminator 3, and on the fluorescent characteristics of the illuminated markers 40, at least some of these markers 40 may become "excited" (i.e., fluoresce) in response to being illuminated, and emit resulting, characteristic fluorescent radiation wavelengths (also referred to as "emission wavelengths" for convenience). Examples of various emission wavelengths yielded by the various ones of the markers shown in the first column of FIGS. 3a and 3b, in response to being "excited" by various source illuminator "excitation" wavelengths shown in a second column of FIGS. 3a and 3b, are shown in a third column of FIGS. 3a and 3b. As can be appreciated in view of the third column of the table of FIGS. 3a and 3b, some markers may emit substantially similar wavelengths (e.g., markers Lucifer Yellow CH, Calcium Green, and Toto-1 have emission wavelengths of 533 nm in response to being illuminated by the respective excitation wavelengths shown in column 2). A fourth column of FIGS. 3a and 3b also shows the differences between the excitation wavelengths and emission wavelengths corresponding to respective ones of the markers of FIGS. 3a and 3b.

Any emission wavelengths that are yielded by the markers 40 from sample 4a as a result of being illuminated by one or more of the slit images from one or more of the slit image groups 14a"–14c" are directed as radiation beams to a beam splitter 15, via the objective 16. The beam splitter 15 splits these beams, and portions of these beams become radiation beam portions 44 which are focussed by the beam splitter 15 to portions of a monochrometer slit optic 19 (also referred to as "slit optic 19" for convenience). The slit optic 19 has a similar configuration as the mask 14 described above and shown in FIG. 7, and thus will not be described in further detail, although it should be noted the beam splitter 15 and slit optic 19 are preferably positioned so that any wavelengths emitted by one or more of the markers 40 in response to being illuminated by beams output from one or more slits 14d of mask 14, are focussed by beam splitter 15 to corresponding slits of slit optic 19.

At the slit optic 19, each individual one of the slits of the slit optic 19 that receives a radiation beam portion 44 from the beam splitter 15 transmits the received radiation beam portion 44 to a collimating lens 19'. The beam portions transmitted by the various slits of slit optic 19 are hereinafter collectively referred to as beams 19". The collimating lens 19' collimates the beams 19" received from the slit optic 19 and provides a resultant, collimated beam 20' to a grating 20.

The grating 20 diffracts the collimated beam 20' so as to separate the wavelengths of the collimated beam 20' into predetermined wavelength bands. The grating 20 is mounted on a fixed angle pedestal 20a, the angle (θ2) of which is selected so that selected wavelengths are diffracted from the grating 20 and directed to a focussing optic 22 which, in turn, directs respective ones of these wavelengths to respective rows of a radiation-sensitive surface 25a of a two-dimensional detector array 25 (i.e., a photodetector array). Depending on applicable performance criteria, the grating 20 and angle (θ2) may be selected to as to provide a required separation (i.e., segregation) of wavelengths into either narrow or wide wavelength bands.

In accordance with a preferred embodiment of the invention, the surface 25a of detector array 25 includes a plurality of rows (I) and a plurality of columns (J) of radiation detector elements. Preferably, the surface 25a includes 256 or more rows (I) and 256 or more columns (J) of radiation detector elements. As can be seen in view of FIG. 8, the rows (I) include a first group of rows of detector elements (G1), a second group of rows of detector elements (G2), and a third group of rows of detector elements (G3). Each individual one of these groups of rows (G1), (G2), and (G3) preferably includes 85 rows of radiation detector elements. In the preferred embodiment of the invention, the configuration of the components 20 and 22 is such that 1) the rows of detector elements from the first group (G1) detect wavelengths emitted from one or more markers 40 of the sample 4a as a result of the markers being illuminated by slit images from slit image group 14a'', 2) the rows of detector elements from the second group (G2) detect wavelengths emitted by one or more markers 40 from sample 4a as a result of the markers being illuminated by slit images from slit image group 14b'', and 3) the rows of detector elements from the third group (G3) detect wavelengths emitted by one or more markers 40 from sample 4a as a result of the markers being illuminated by slit images from slit image group 14c''. Within each group (G1), (G2), and (G3), each row of radiation detector elements within the group receives, and corresponds to, a respective range of wavelengths. By example, and referring again to the grating 20 and the focussing optic 22, the grating preferably operates in combination with the focussing optic 22 so as to direct marker emission wavelengths within an approximate range from 405 nm to 661 nm to each group of rows (G1), (G2), and (G3) of the detector array surface 25a, wherein the wavelengths directed to the groups (G1), (G2), and (G3) correspond to slit image groups 14a'', 14b'', and 14c'', respectively. More particularly, and according to a preferred embodiment of the invention, the grating 20 preferably operates in combination with the focussing optic 22 to direct any wavelengths that are emitted as a result of slit image group 14a'' illuminating the sample slide 4, and which are in the range from Knm to (K+2)nm, to a corresponding Nth one of the rows of group (G1), where K=405, 408, 411 . . . 658, for corresponding values of N=1, 2, 3 . . . 256. Similarly, the grating 20, in combination with the focussing optic 22, directs any wavelengths that are emitted as a result of slit image group 14b'' illuminating the sample slide 4, and which are in the range from Knm and (K+2)nm, to a corresponding Nth one of the rows of group (G2), where K=405, 408, 411 . . . 658, for corresponding values of N=1, 2, 3 . . . 256. Moreover, the grating 20, in combination with the focussing optic 22, directs any wavelengths that are emitted as a result of slit image group 14c'' illuminating the sample slide 4, and which are in the range from Knm to (K+2)nm, to a corresponding Nth one of the rows of group (G3), where K=405, 408, 411 . . . 658, for corresponding values of N=1, 2, 3 . . . 256.

Figure 8:
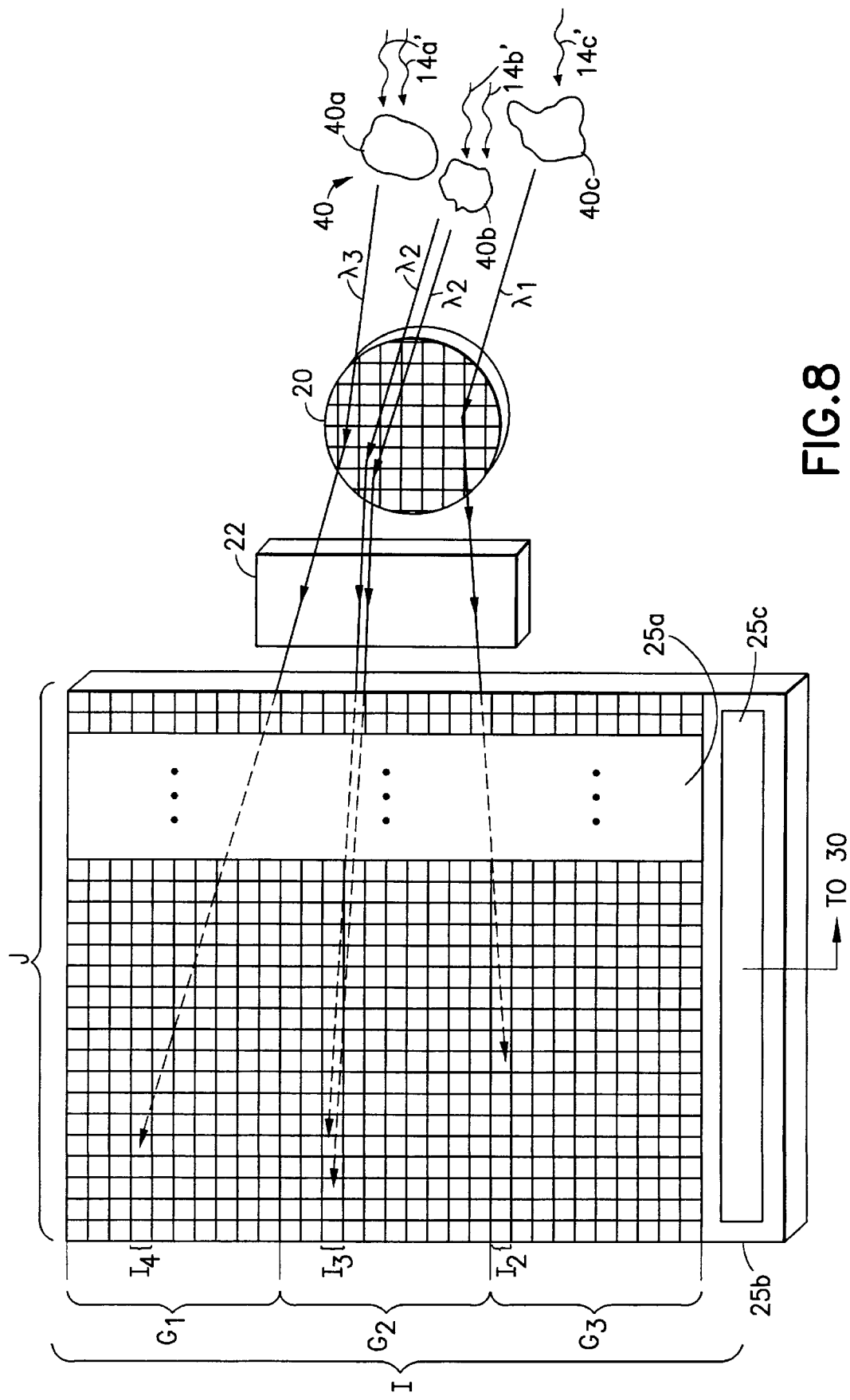
FIG. 8 shows a perspective view of a grating 20, a surface 25a of a detector array 25, and a focussing optic 22, all of which are components of the imaging system of FIGS. 1a and 1c, and of the imaging system of FIGS. 1b and 1c, wherein FIG. 8 further shows various fluorescent materials 40a–40c and exemplary emission wavelengths of these fluorescent materials.

This may be further understood in view of FIG. 8, which shows a perspective view of the grating 20, the surface 25a of the detector array 25, various ones of the markers 40 (the various markers are further referenced by labels "40a'", "40b'", and "40c'") from sample 4a, and also exemplary emission wavelengths (e.g., λ1=406 nm, λ2=412 nm, and λ3=415 nm) that are yielded by the markers 40a, 40b, and 40c in response to being illuminated by one or more beams from respective ones of the groups of slit image beams 14a', 14b', and 14c'. As can be appreciated in view of FIG. 8, the wavelengths (λ1, λ2, λ3) emitted by the respective markers 40c, 40b, and 40a in response being illuminated by the beams from the respective slit image beam groups 14c', 14b', and 14a' are diffracted by the grating 20, and are then directed through focussing optic 22 to a corresponding radiation detector element of a corresponding row (I1), (I3), (I4) of a respective one of the group of rows (G3), (G2), and (G1). Also, within each row of the respective groups (G1), (G2), and (G3), wavelengths received by radiation detector elements of the row correspond to the respective individual slit images of the corresponding slit image groups 14a'', 14b'', and 14c'' which caused the markers to emit the wavelengths.

The detector array 25 will now be described in further detail. The detector array 25 may be constructed in accordance with charge coupled device (CCD) technology, although the teaching of this invention is not limited for use only with CCD imaging arrays. One suitable embodiment for the detector array 25 includes a Single Frame Gated Optical Imager manufactured by Kentech Instruments, Ltd.

The marker emission wavelengths incident on the surface 25a of the detector array 25 produce corresponding charge images in potential wells of the detector array 25. That is, the reception of the wavelengths results in the generation of corresponding charge packets or charge images within the potential wells of the detector array 25. The detector array 25 also includes a readout 25b that includes an internal gate array 25c. The gate array 25c is controllable by the control processor 30 for being either 'enabled' (during sampling times) or 'disabled' (during other, non-sampling times). During times when the gate array 25c is enabled, the readout 25b of the detector array 25 provides, on a row-by-row basis, output signals corresponding to the wavelengths detected by the radiation detector elements of the respective rows (I). These output signals, which represent image information, are forwarded to the control processor 30 (FIG. 1c) which processes the signals in a manner as will be described below.

Before describing a method of the invention, reference will first be made to a memory 31, frame stores F1–F4, and to tables T1 and T2 of the imaging system 1 of the invention. The memory 31 stores various constants and variables that are used by the control processor 30 during the operation of the imaging system 1. By example, the memory 31 stores a value of a variable $T_P$. The value of variable $T_P$ specifies a first predetermined time period value, and is employed by the control processor 30 in a manner as will be described below. Also by example, the memory 31 stores a value for a variable "STEP". The variable STEP represents a number of a "step" kept by a counter 30a of the control processor 30, where a "step" includes a complete movement or increment of the sample slide 4 along axis (x) (on stage 18) by a predetermined distance. The value of variable STEP is updated by the counter 30a for each "step" of the sample slide 4, as will be described below. The memory 31 further stores a variable PF which is employed during a "high resolution operating mode" of the invention to identify the number of times the source illuminator 3 has fired a pulse beam, as will also be described below. An operating program for controlling the operation of the control processor 30 is also stored in the memory 31.

Figure 13:
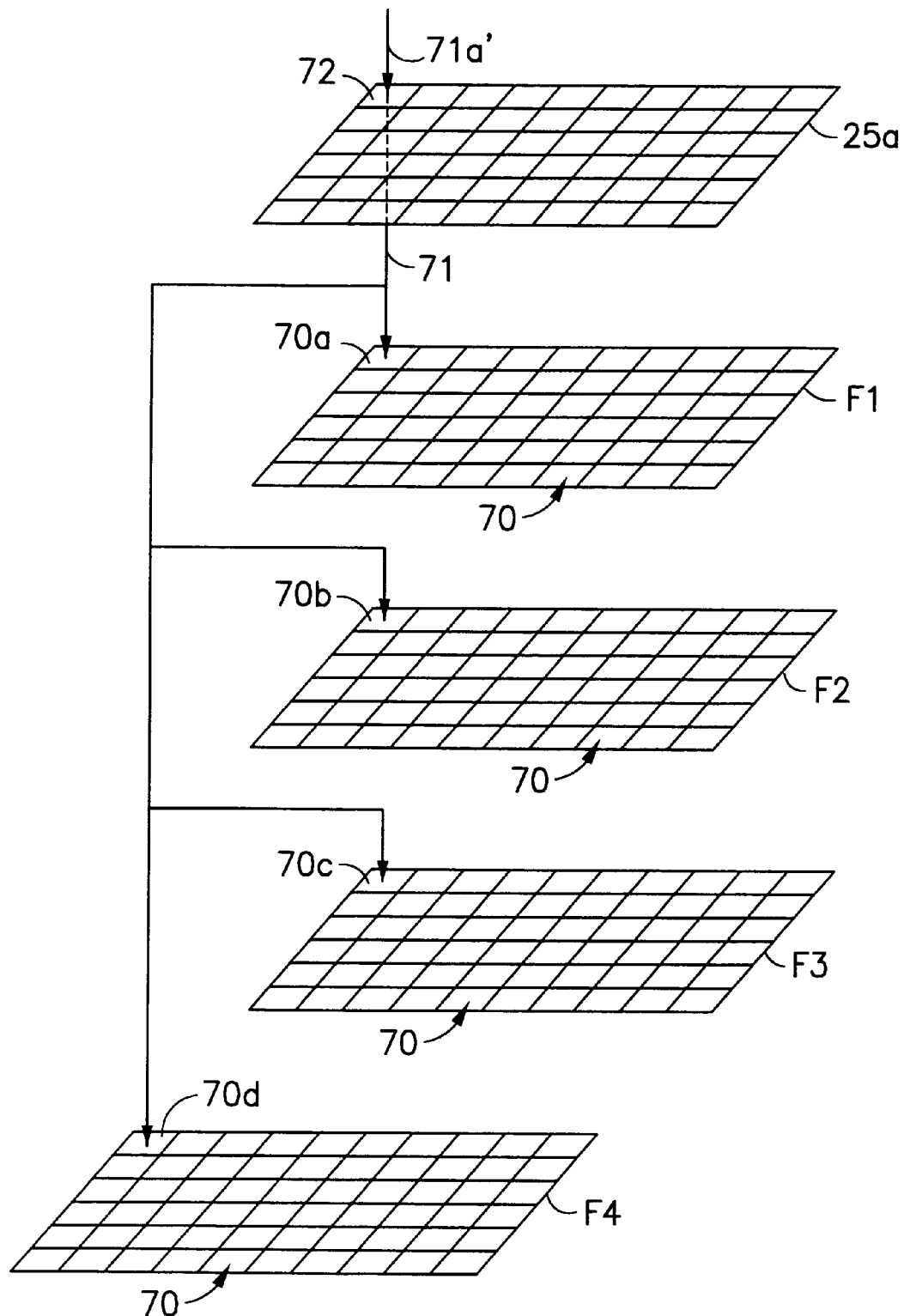
FIG. 13 shows a perspective view of a surface 25a of the detector array 25 of FIG. 8, and also shows a perspective view of frame stores F1–F4 of the imaging system of FIGS. 1a and 1b, and of the imaging system of FIGS. 1b and 1c.

The frame stores F1–F4 are employed while the system 1 is operating in the "high resolution operating mode" to store signals that are output from detector array 25 during respective ones of a plurality of sampling time periods, and which are determined to exceed a predetermined threshold level. Referring to FIG. 13, each frame store F1–F4 includes a respective array of storage bins 70. Each of these storage bins 70 corresponds to a particular one of the radiation detector elements of the surface 25a of the detector array 25. Thus, during a first one of the sampling times, for each respective signal that is output by the detector array 25 and which is determined to have an amplitude exceeding the predetermined threshold level, the signal is stored in a particular storage bin 70 within frame store F1 corresponding to a particular radiation detector element (from a particular row (I) and column (J) of the surface 25a) which detected the wavelength corresponding to the signal. Similarly, during second, third, and fourth sampling times, for each respective signal that is output by the detector array 25 and which is determined to have an amplitude exceeding the predetermined threshold level, the signal is stored in a particular storage bin 70 within frame store F2, frame store F3, and frame store F4, respectively, wherein the storage bin 70 corresponds to a particular radiation detector element (from a particular row (I) and column (J) of the surface 25a) which detected the wavelength corresponding to the signal. The sampling time periods will be described in detail below. FIG. 13 shows an exemplary representation of a signal 71 output by the detector array 25 to storage bins 70a–70d of the respective frame stores F1–F4 during the respective sampling periods, in response to a particular detector element 72 of the surface 25a of the detector array 25 receiving an emission wavelength 71a' during these respective sampling periods.

Figure 14:
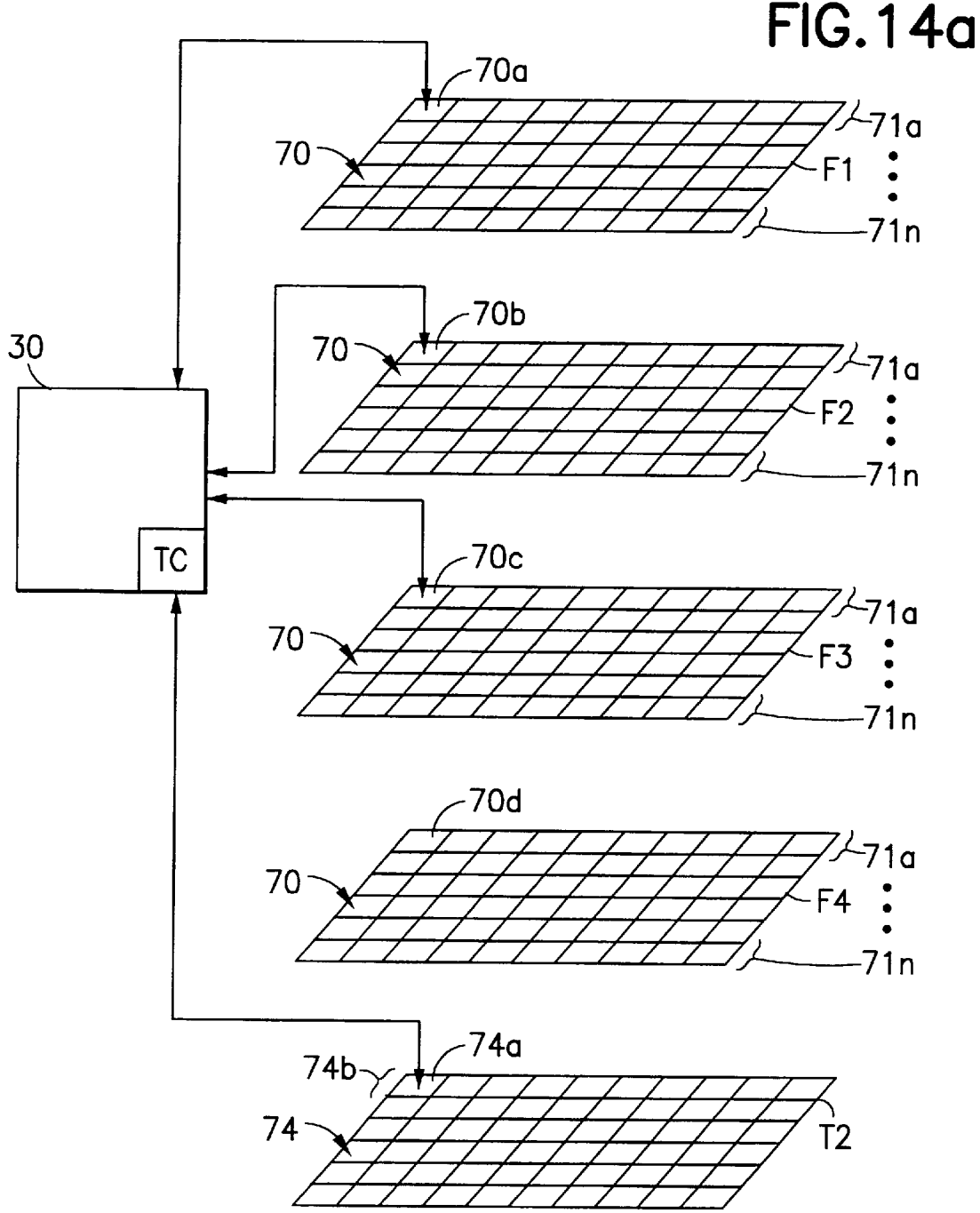
FIG. 14a shows a table T1 of the portion of the imaging systems of FIG. 1b, wherein table T1 stores information for use in accordance with a method of the invention.
FIG. 14b shows a perspective view of the frame stores F1–F4 of FIG. 13, and also shows a perspective view of a table T2 of the imaging system of FIGS. 1a and 1b, and of the imaging system of FIGS. 1b and 1c, wherein the table T2 stores calculated marker emission decay time constant values in accordance with this invention.

Reference is now made to the table T1 (which is preferably a look-up table), which is shown in greater detail in FIG. 14a. Table T1 stores various types of information that is employed by the control processor 30 while performing a technique in accordance with the invention for determining which types of markers and/or proteins, if any, are included in the sample 4a. By example, and in accordance with one embodiment of the invention, the table T1 stores information identifying particular types of markers that are employed during examination of the sample 4a. Also by example, and in accordance with another embodiment of the invention, the table T1 also stores information identifying particular types of proteins the sample 4a is being tested for. The table T1 also stores information defining reference values of characteristic wavelengths that are emitted by these markers in response to being "excited" by specific excitation wavelengths (from source illuminator 3). The table T1 further stores information defining reference fluorescent decay time constant values associated with these emission wavelengths. Examples of various types of markers and their associated emission wavelengths and emission wavelength (fluorescent) decay time constants are shown in columns 1, 3, 5, respectively, of FIGS. 3a and 3b. That is, the table Ti is assumed to store at least the information shown in FIGS. 3a and 3b.

The information identifying the markers employed in sample 4a and the characteristic emission wavelengths of these markers corresponds to respective ones of rows 71a–71n of storage bins 70 within the frame stores F1–F4. By example, row 71a of the respective frame stores F1–F4 (which include respective storage bins 70a–70d) may correspond to a specific band of wavelengths, such as a that from 405 nm to 407 nm. Assuming that the information stored in table T1 includes information specifying marker INDO 1 (see column 1 of FIG. 3a), which has a characteristic emission wavelength of 405 nm when illuminated with an excitation wavelength of 335 nm, then the information specifying the marker INDO1 and the corresponding emission wavelength of 405 nm corresponds to the row 71a of storage bins 70 of the respective frame stores F1–F4. This is assumed to be known by the control processor 30.

Reference is now made to the table T2. The table T2 is employed by the control processor 30 during the operation of the imaging system 1 to store calculated decay time constant information. Referring to FIG. 14b, the table T2 (i.e., a look-up table) preferably includes an array of storage bins 74, each of which corresponds to a particular one of the storage bins 70 of each respective one of the frame stores F1–F4. After the control processor 30 calculates decay time constants for signals stored in corresponding storage bins 70 within frame stores F1–F4, time constant information is stored in a corresponding storage bin 74 within table T2, as will be further described below.

Reference is now made to FIGS. 4a–5d which illustrate a flow diagram of a method in accordance with this invention. The method includes various modes of operation, namely, an "initial screening mode" and the "high resolution operating mode", which is comprised of sub-modes, including a "spectral analysis mode" and a "temporal analysis mode". Each of these operating modes will be described in detail below.

Figures 1C, 1E:
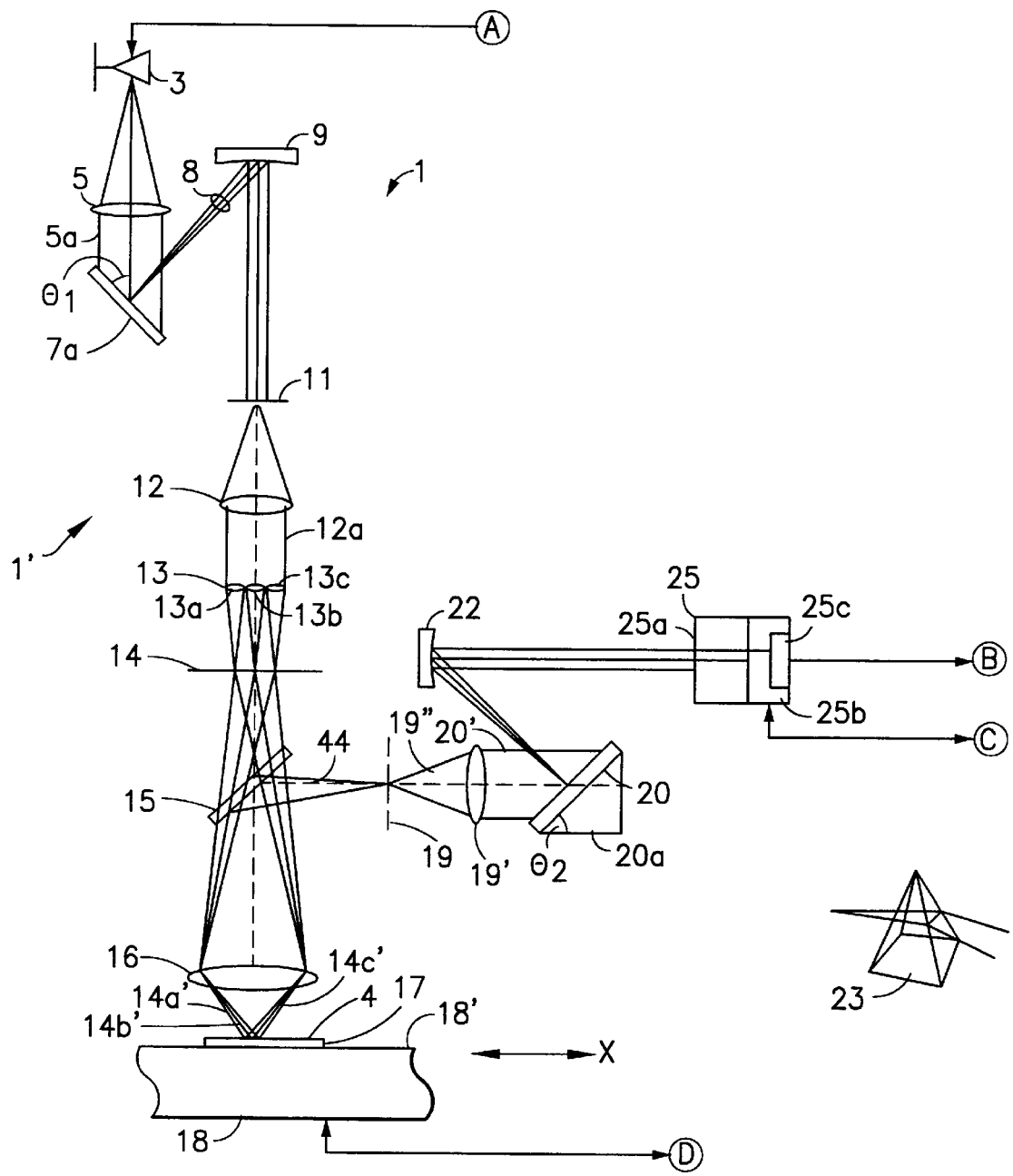
FIG. 1c shows a portion of an imaging system that is constructed in accordance with another embodiment of the invention, wherein the imaging system in accordance with this embodiment of the invention includes the components shown in FIGS. 1c and 1b.
FIG. 1e shows the manner in which FIGS. 1b and 1c relate to one another.
Figure 4A:
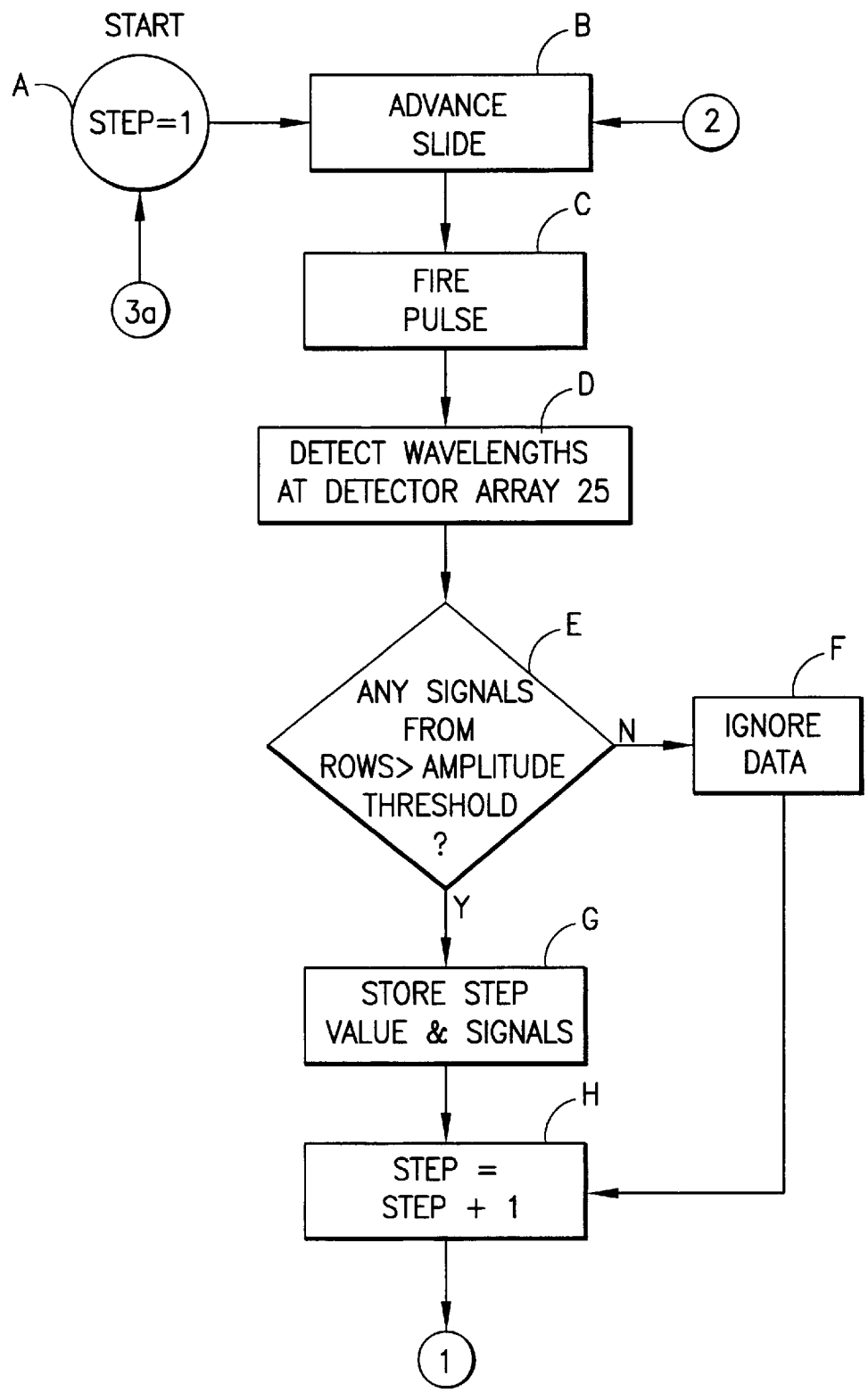
FIGS. 4a and 4b show a flow diagram depicting a portion of a method of this invention.
Figure 4B:
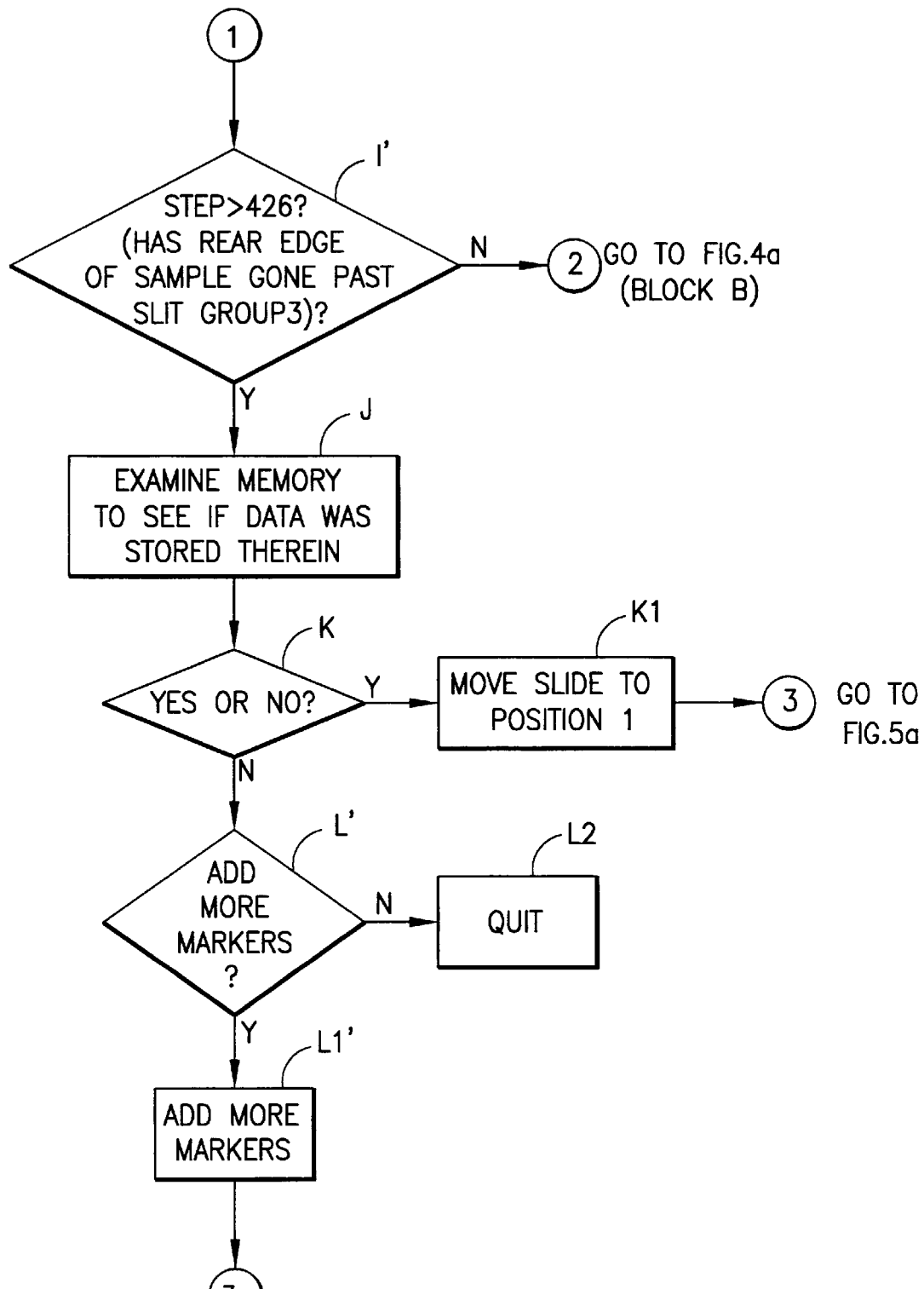

FIGS. 4a and 4b represent a portion of the method that is referred to the "initial screening mode". In this mode, the sample 4a is initially "screened" or examined for the presence of proteins that are known to be associated with a particular type of cancer for which the sample 4a is being tested. By example only, and as is known in the art, the presence of any one of a RAS protein, a P53 protein, and a BRCA1 protein, in a tissue sample indicates with approximately 70% accuracy that there are cancerous cells (e.g., breast cancer) included in the sample. Thus, for the purposes of this description, it is assumed that the initial screening mode is performed so as to examine the sample 4a for the presence of any one of these proteins, and that the sample 4a has been provided with three corresponding types of fluorescent markers 40a, 40b, and 40c, which, assuming the sample 4a includes cancerous cells, emit characteristic radiation wavelengths in response to being illuminated by specific wavelengths. By example only, it is assumed that the sample 4a has been provided with markers such as Fluoroscene or Fluo-3, which are each typically used to detect the presence of the RAS protein, Rhodamine 123, which is typically used to detect the presence of the P53 protein, and CY3 or CY5, which are each typically used to detect the presence of the protein BRCA1. Also for the purposes of this description, it is assumed that it is desired to examine the sample 4a for the presence of any of the three proteins simultaneously. It is further assumed that the embodiment of the imaging system 1' shown in FIGS. 1c and 1b is employed to perform the method of the invention, although it should be noted that in other cases where it is desired to examine the sample 4a using only a single, selected excitation wavelength at a time, the imaging system 1 of FIGS. 1a and 1c may be employed. It should further be noted that in other suitable cases, one or more other selected types of markers may be included in the sample, depending on which types of proteins the sample 4a is being tested for.

Figure 2B:
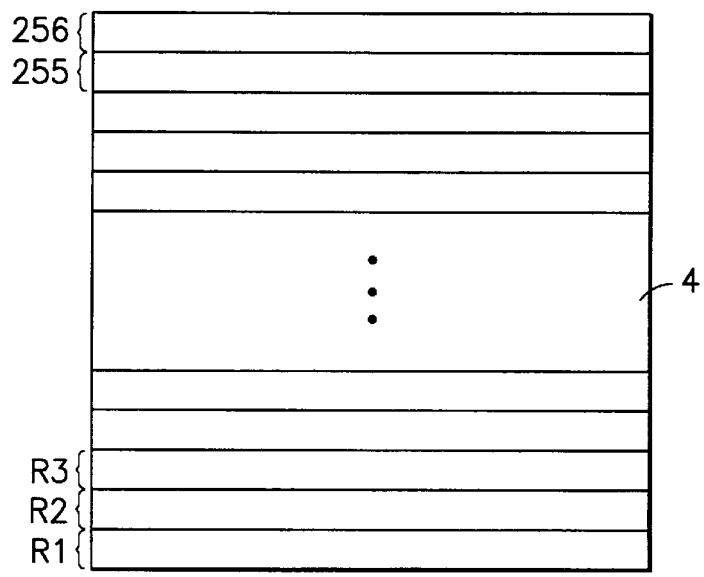
FIG. 2b shows the sample slide 4 of FIG. 2a, wherein imaginary rows are superimposed over the sample slide 4.

For the purposes of convenience only, in the following description it is assumed that the sample slide 4 (FIG. 2a) has a length (L1) which is approximately equal to the product of 256×(W1), where, as was previously described, (W1) represents the width of individual ones of the slit rows 14a–14c of mask 14. It is also assumed that the width (W2) of the sample slide 4 is approximately equal to the product of 256×(L), where, as was also previously described, (L) represents the length of individual ones of the slits of the slit rows 14a–14c of mask 14. As such, it can be said that the sample slide 4 includes 256 "rows", each having a width (W1), and 256 "columns", wherein each column has a length (L). FIG. 2b shows the sample slide 4, over which imaginary rows R1–R256 are superimposed for convenience.

Figure 9A:
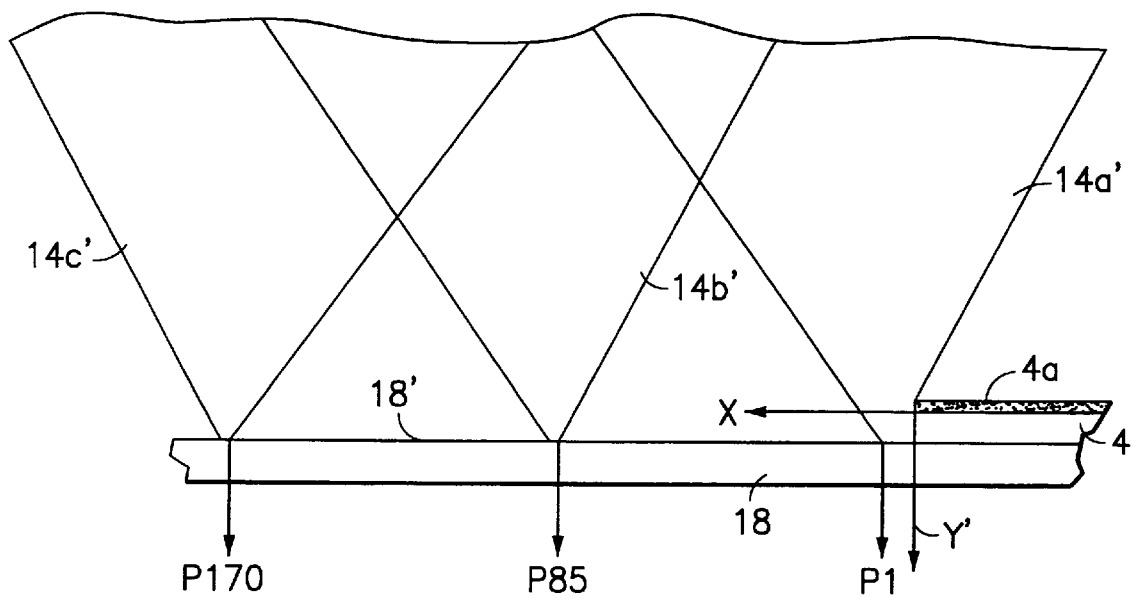
FIGS. 9a–9g show a side view of the sample slide 4 of FIGS. 2a and 2b disposed over a stage 18 of FIGS. 1a and 1c, and also shows slit image beams 14a'–14c' generated within the imaging systems for illuminating the sample slide 4, wherein the sample slide 4 is positioned at various locations on the stage 18 throughout FIGS. 9a–9g.

Referring again to FIG. 4a, at block A the method is started, and the variable "STEP" from memory 31 is initialized to a value "1". As was previously described, the variable STEP represents a "step" number kept by the counter 30a of the control processor 30, where a "step" includes a complete advancement or displacement of the sample slide 4 along axis (x) by a predetermined distance. For the purposes of this description, it is assumed that the predetermined distance is equivalent to width (W1). More particularly, for the purposes of this description it is assumed that each "step" includes a complete displacement of the sample slide 4 by a distance that is equivalent to the width (W1) of an individual "row" of the sample slide 4. It is also assumed that each "step" places a front edge 4a' of the sample slide 4 at a corresponding position or location on the stage 18 relative to an axis y' (shown in FIGS. 9a–9f). By example, FIGS. 9a and 10a show the sample slide 4 disposed on the stage 18, where edge 4a' of the slide 4 is positioned parallel to the axis y'. Also by example, and assuming that the sample slide 4 is subsequently advanced by a total of 426 individual "steps", each of these steps places the edge 4a' of the sample slide 4 at a corresponding one of 426 different locations relative to the axis y'. These locations are hereinafter referred to as locations or positions P1–P426, respectively.

Also, at block A it is assumed that the sample slide 4 is disposed on the upper surface 18' of the stage 18 so that edge 4a' of the slide 4 is parallel to axis y', as is depicted in FIGS. 9a and 10a. As can be appreciated in view of FIGS. 9a and 10a, the position of the sample slide 4 is such that, assuming a pulse beam were to be fired from source illuminator 3, beams from the respective slit image beam groups 14a'–14c' would not illuminate the slide 4, but would instead illuminate upper surface 18' of the stage 18.

At block B, and as a first step in the advancement of the sample slide 4, the control processor 30 controls the stage 18 so as to advance the sample slide 4 along the axis (x) by a distance that is substantially equivalent to width (W1) (i.e., by a distance that is substantially equivalent to width (W1) of a "row" of the sample slide 4). The advancement of the sample slide 4 causes the edge 4a' of the sample slide 4 to reach a position P1 on the stage 18 relative to axis y'. Thereafter, at block C the control processor 30 controls the source illuminator 3 so as to cause the source illuminator 3 to fire a single pulse beam of a selected broad band of wavelengths. Preferably, the wavelengths of the pulse beam include those which are known to "excite" respective ones of the markers 40a–40c employed in the sample 4a, causing the marker(s) to emit corresponding fluorescent radiation. Also, it is assumed that the components 5, 7a, 9, and 11 are configured so as to enable these wavelengths to be provided through the slit 11 for illuminating the sample slide 4.

Figure 9B:
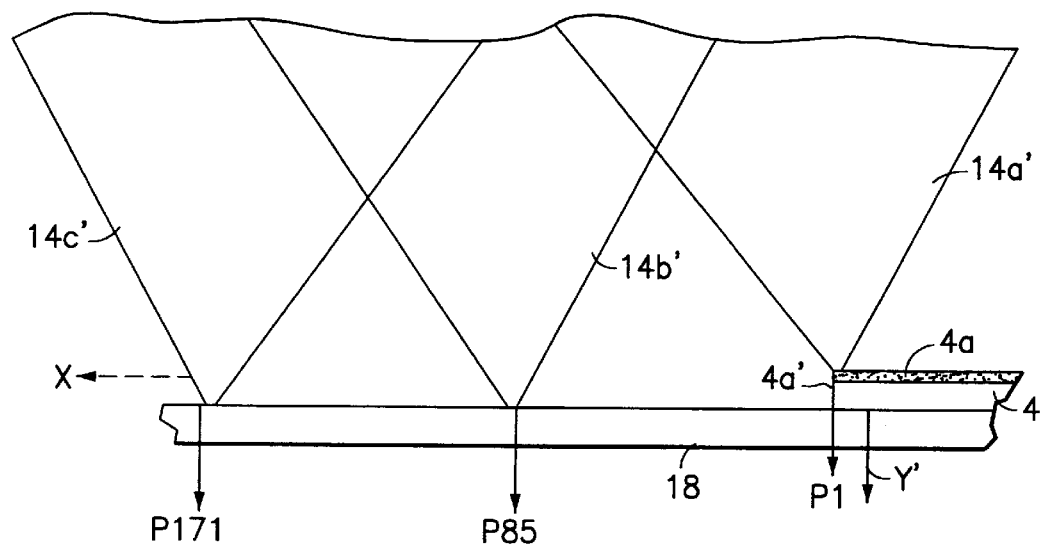
Figure 9C:
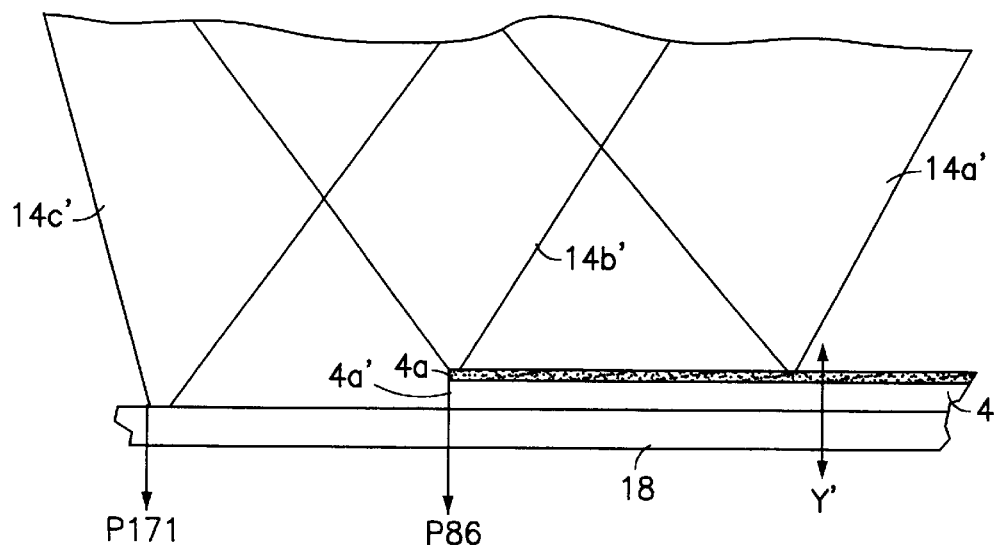
Figure 9H:
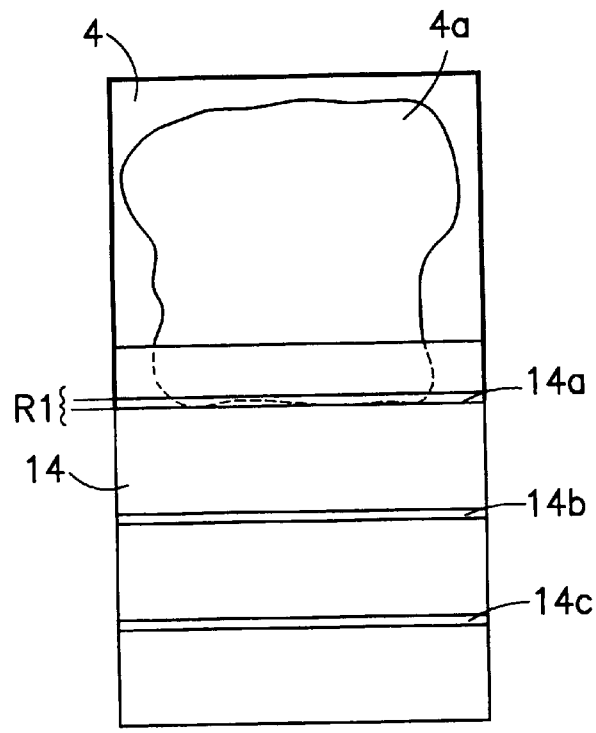
FIGS. 9h–9k show a perspective view of the mask 14 of FIG. 7, and also shows the sample slide 4 in positions corresponding to those of the slide 4 shown in FIGS. 9b, 9c, 9d, and 9f, respectively.
Figure 10A:
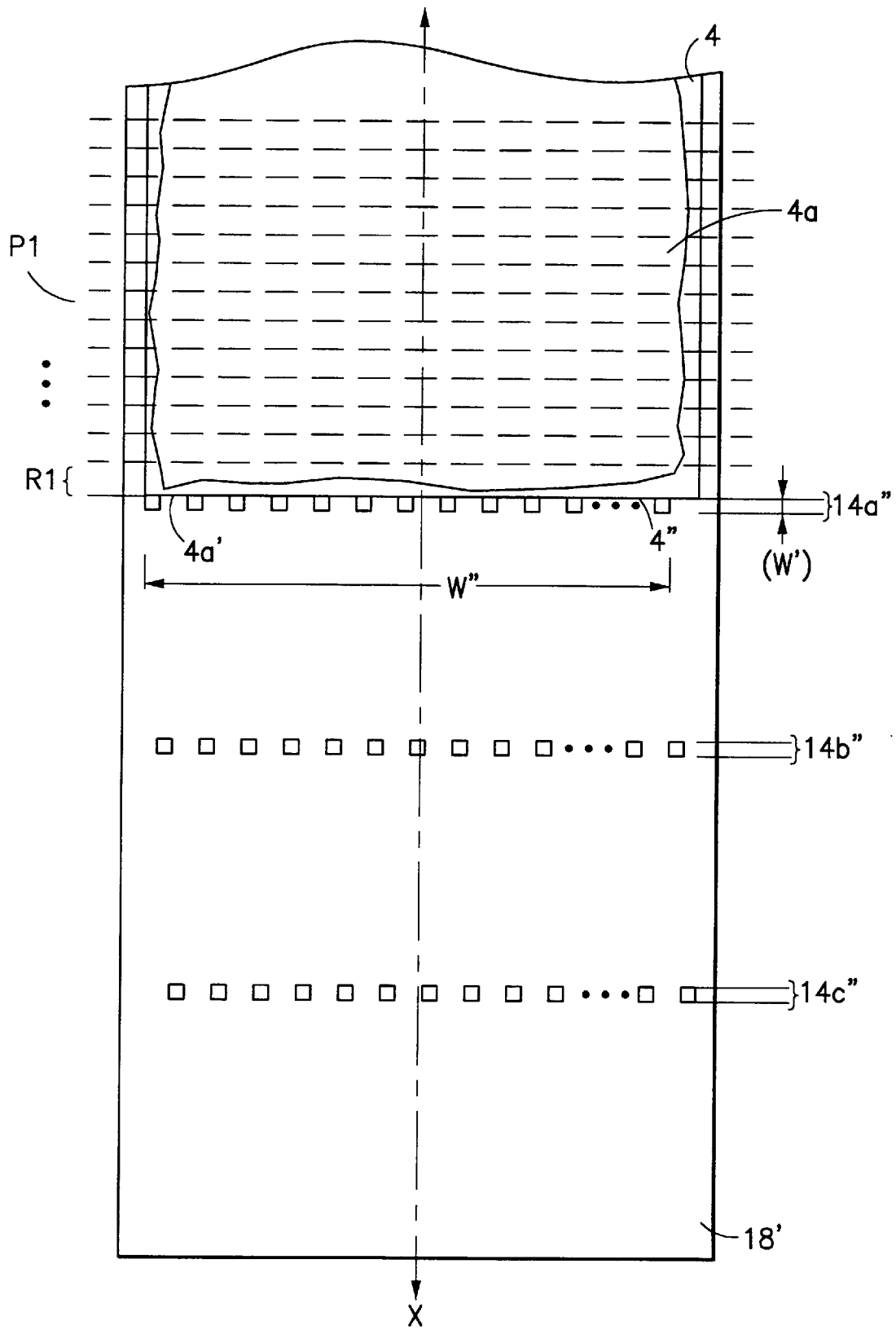
FIGS. 10a–10g show the sample slide 4 and stage 18 of FIGS. 9a–9g, as viewed from a perspective looking down on the sample slide 4 and stage 18, and further shows slit image groups 14a''–14c'' that appear on the sample slide 4 as a result of the slit image beams 14a'–14c' of FIGS. 9a–9g illuminating the sample slide 4.
Figure 10B:
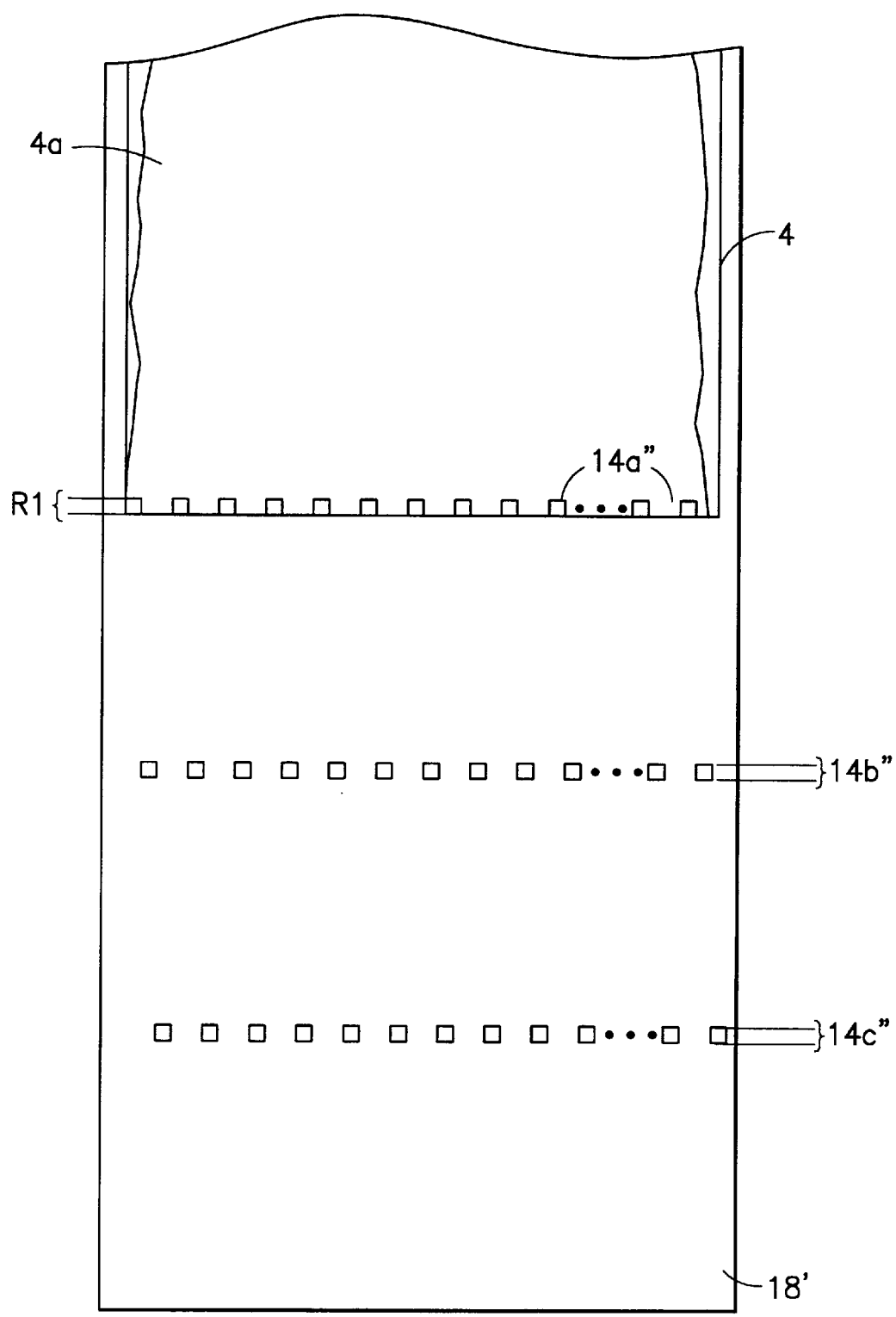

The firing of the pulse beam at block C results in "row" R1 of the sample slide 4 being illuminated by slit images from slit image group 14a'' (which corresponds to slit image beam group 14a'), as may be understood in view of FIGS. 9b and 10b. As can also be appreciated in view of FIGS. 9b and 10b, the firing of the pulse beam at block C results in the upper surface 18' of the stage 18 being illuminated by the slit image beam groups 14b' and 14c' corresponding to slit image groups 14b'' and 14c''. This can also be seen in view of FIG. 9h which shows a perspective view of a portion of the mask 14, and the slide 4 disposed over the upper surface 18' of the stage 18.

At block D the radiation detection elements of the surface 25a of detector array 25 detect radiation resulting from the slit images 14a'' illuminating the sample slide 4 (and the slit images 14b''–14c'' illuminating surface 18' of stage 18), in the manner described above. Assuming that the gate array 25c is 'enabled' by the control processor 30, the readout 25b of detector array 25 then provides, on a row-by-row basis, output signals to the control processor 30, where, as was previously described, the signals from each row correspond to a respective band of wavelengths received by detector array 25.

Within the control processor 30, as each output signal from the detector array 25 is received, the amplitude of the signal is detected using, in accordance with a preferred embodiment of the invention, an A/D converter block 30c. Then, the detected amplitude of each signal is compared to a predetermined threshold level until it is determined that at least one of the detected amplitudes, if any, exceeds the predetermined threshold level (block E). If it is determined at block E that the amplitudes of none of the signals exceed the predetermined threshold level ('no' at block E), then all of the signals are ignored by the control processor 30 at block F, and control passes through connector 1 to block H, which will be described below.

It should be noted that the predetermined threshold level may be specified by a user of the CPU 30', using keypad 33. Preferably, the predetermined threshold level is greater than the amplitude level of any ambient wavelengths that may be detected by the detector array 25, including, by example, any wavelengths that may be generated as a result of the slit image beam groups 14b' and 14c' illuminating the upper surface 18' of stage 18 rather than sample slide 4. In this manner, any wavelengths that may be detected by the detector array 24 as a result of any of the slit image beam groups 14b' and 14c' not illuminating the sample slide 4 are ignored by the CPU 30.

Upon the control processor 30 determining that one or more of the signals received from the detector array 25 exceeds the predetermined threshold level at block E, the control processor 30 stores the value of variable STEP (e.g., value "1") in memory 31. Also, those signals which are determined to have amplitudes exceeding the predetermined threshold level are stored by the control processor 30 in corresponding storage bins 70 within frame store F1. Control then passes to block H where the control processor 30 increments the value of variable STEP by "1". Thereafter, control passes through connector 1 to block I' where the control processor 30 determines whether the value of the variable STEP is greater than a predetermined reference value that specifies a step number (i.e., 426) where the sample slide 4 is advanced to a location on the stage 18 where a rear edge 4b' of the slide 4 is parallel with an axis y1' as shown in FIG. 9g, and where the slide 4 is not illuminated by any of the beam portions 14a'–14c'. If 'no' at block I', then control passes through connector 2 back to block B (FIG. 4a) where a second "step" of advancing the slide 4 is performed. That is, at block B the control processor 30 again controls the stage 18 so as to advance the sample slide 4 by a distance that is equivalent to the width (W1)

(i.e., by advancing the slide 4 so that edge 4a' reaches position P2 relative to axis y'). Thereafter, the procedure identified by blocks C–I' is performed in a similar manner as was described above, and is continuously repeated for each of the subsequent advancements of the slide 4 in step numbers 2 through 85 (i.e., for each of the values of STEP between 2 and 85). For any of these "steps" where it is determined that one or more signals output from the detector array 25 to the control processor 30 exceed the predetermined threshold level at block E, the value of variable STEP indicating the "step" number is stored in memory 31, and the signals are stored in respective storage bins 70 of frame store F1. By example, assuming that while the edge 4a' off the sample slide 4 is positioned at respective locations P2, P16, 20, and P85 during respective steps 2, 16, 20, and 85, it is determined that at least one signal output by the detector array 25 exceeds the predetermined threshold level at block E, then the corresponding values "2", "16", "20", and "85", respectively, of the variable STEP are stored in memory 31 at block G.

Figure 9I:
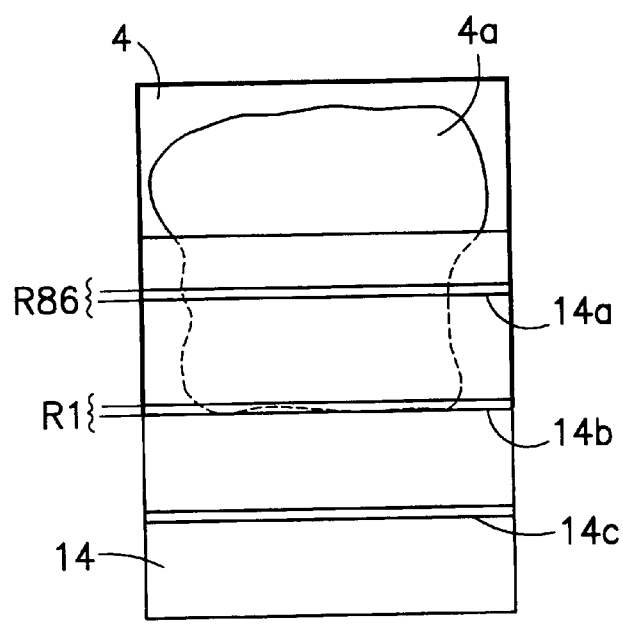
Figure 10C:
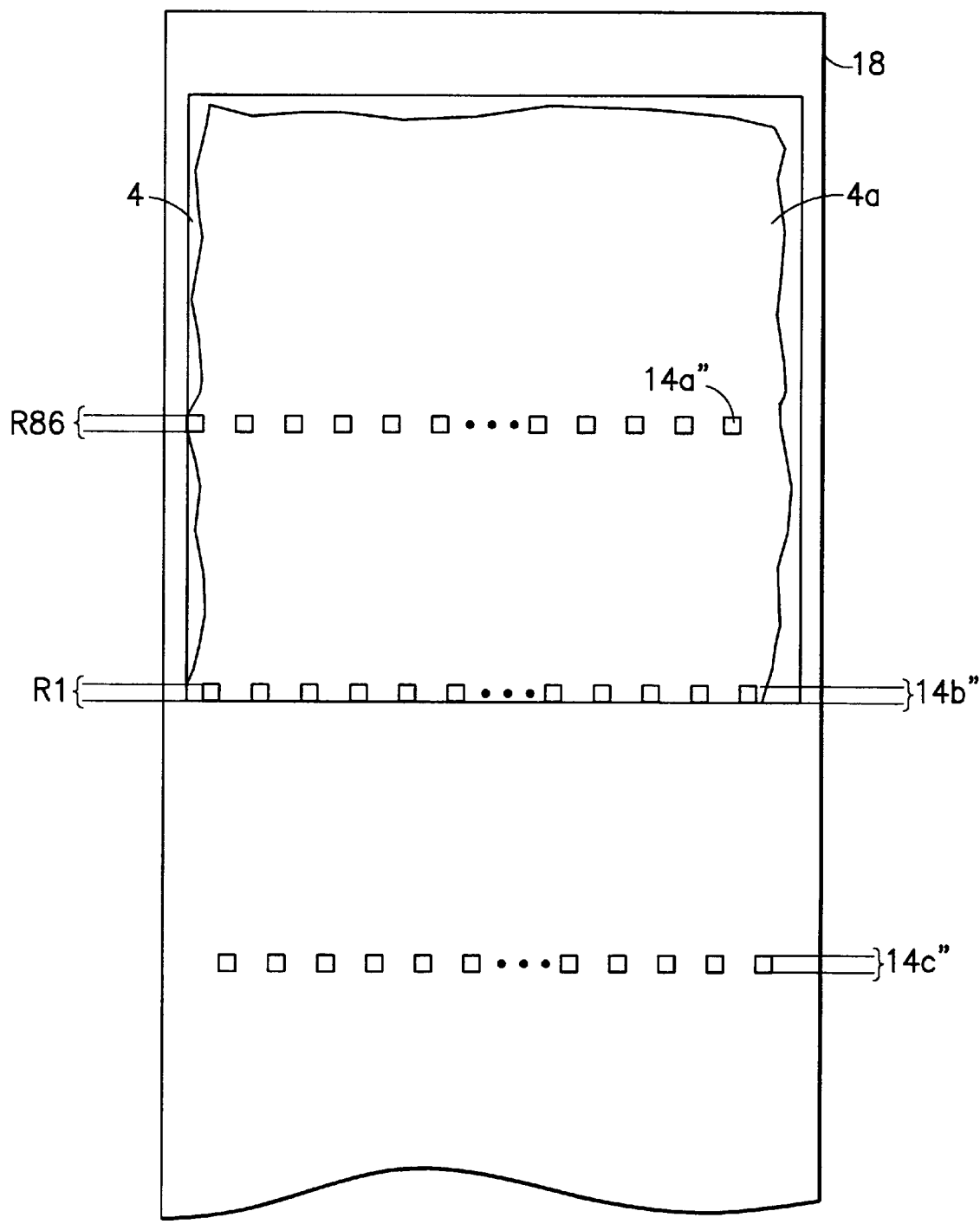

Reference will now be made to the step numbers 86 to 170. It is first assumed that during the performance of the procedure depicted by blocks B-I'0 in FIGS. 4a and 4b, the value of variable STEP reaches the value 86 at block H, and that as a step 86 the sample slide 4 is again advanced at block B by distance (W1) so that edge 4a' reaches location P86. It is also assumed that another pulse beam is fired from the source illuminator 3 at block C. In this case, slit images from both slit image groups 14a" and 14b" illuminate the sample 4a, as may be understood in view of FIGS. 9c and 10c, where FIG. 10c shows rows R1 and R86 being illuminated by slit image groups 14b" and 14a", respectively. This may also be appreciated in view of FIG. 9i which shows a perspective view of a portion of the mask 14, and the sample slide 4, wherein images from slit rows 14b and 14a of the mask 14 illuminate rows R86 and R1, respectively, of the slide 4. For each subsequent advancement of the slide 4 from the position depicted in FIGS. 9c and 10c to a position corresponding to a case where the value of STEP equals 170 (i.e., where the front edge 4a' of the slide 4 reaches location P170), the firing of the pulse beam at block B causes the sample slide 4 to be illuminated by the slit images from both slit image groups 14a" and 14b", but not by slit image group 14c". Any fluorescent emissions that occur as a result of the markers 40a–40c being illuminated by these slit image groups 14a" and 14b" are detected at block D, and the procedures indicated by blocks E–I' are then performed in a similar manner as was described above. For each of the step numbers 86 through 170, assuming that the amplitude of at least one of the signals output by the detector array 25 to the control processor 30 is determined to be greater than the predetermined threshold level at block E, then the value of variable STEP identifying the step number is stored in memory 31 at block G, in a similar manner as was described above.

Figure 9D:
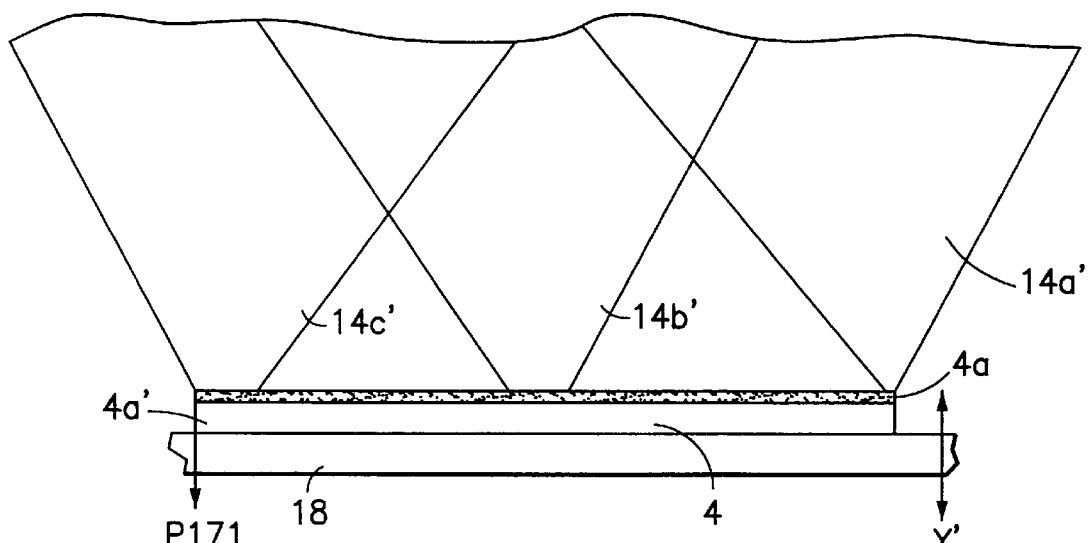
Figure 9E:
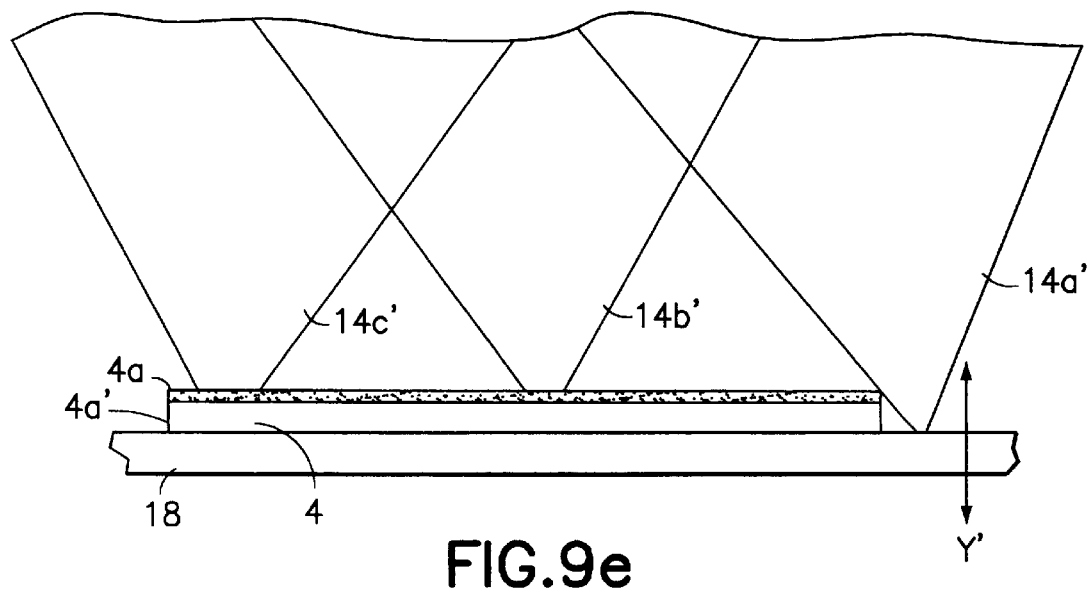
Figure 9F:
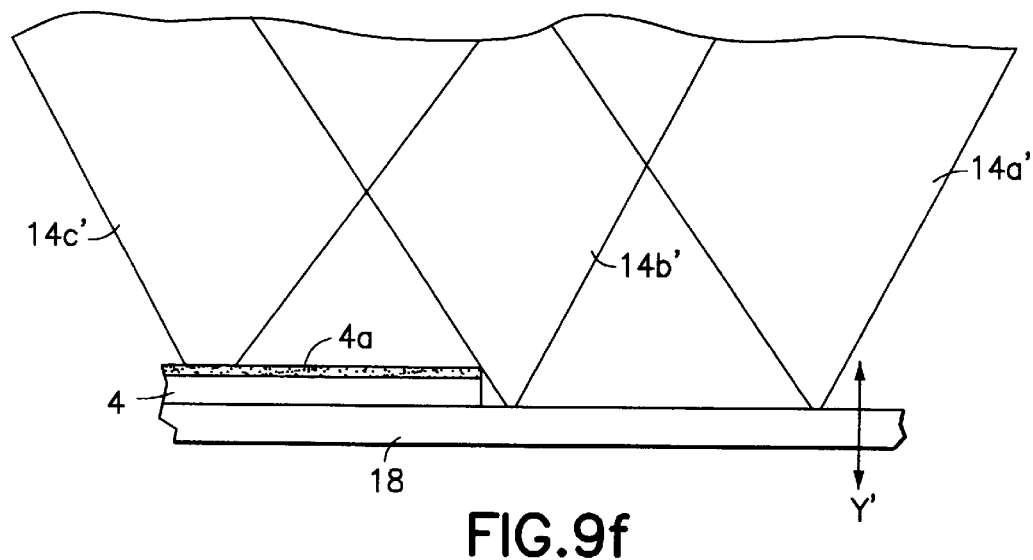
Figure 9G:
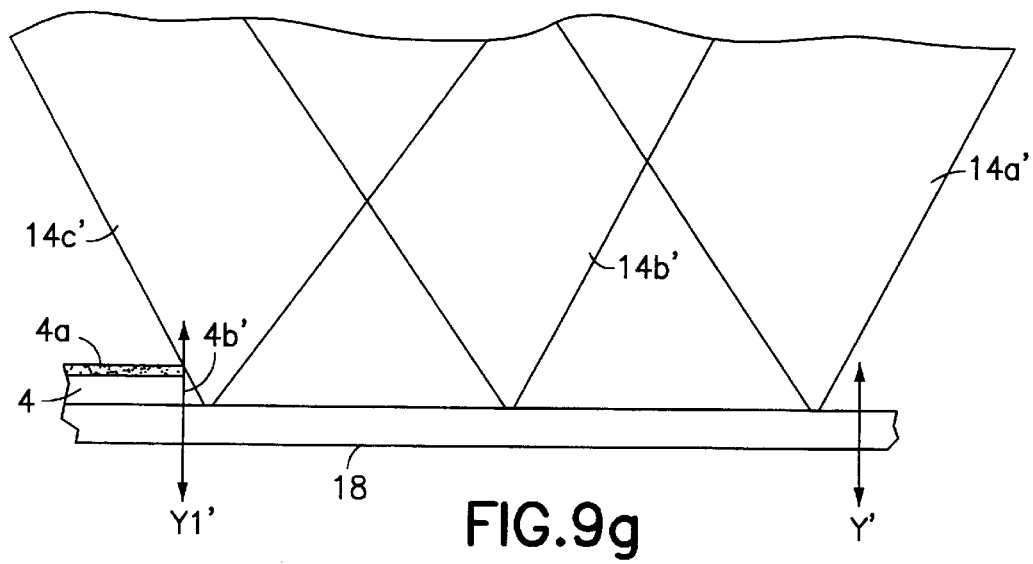
Figure 9J:
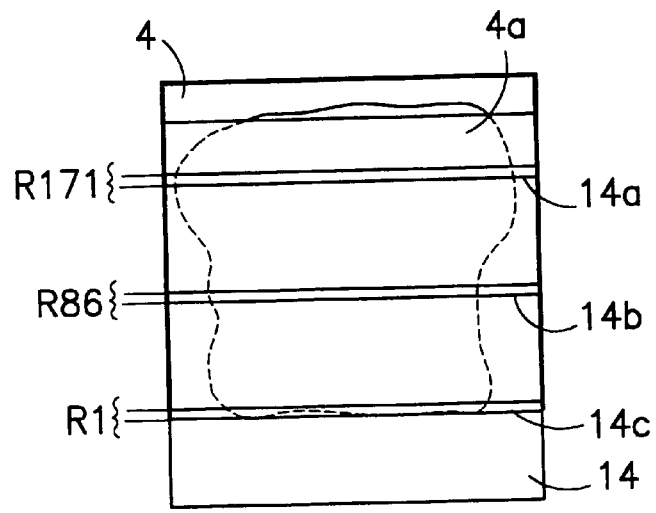
Figure 10D:
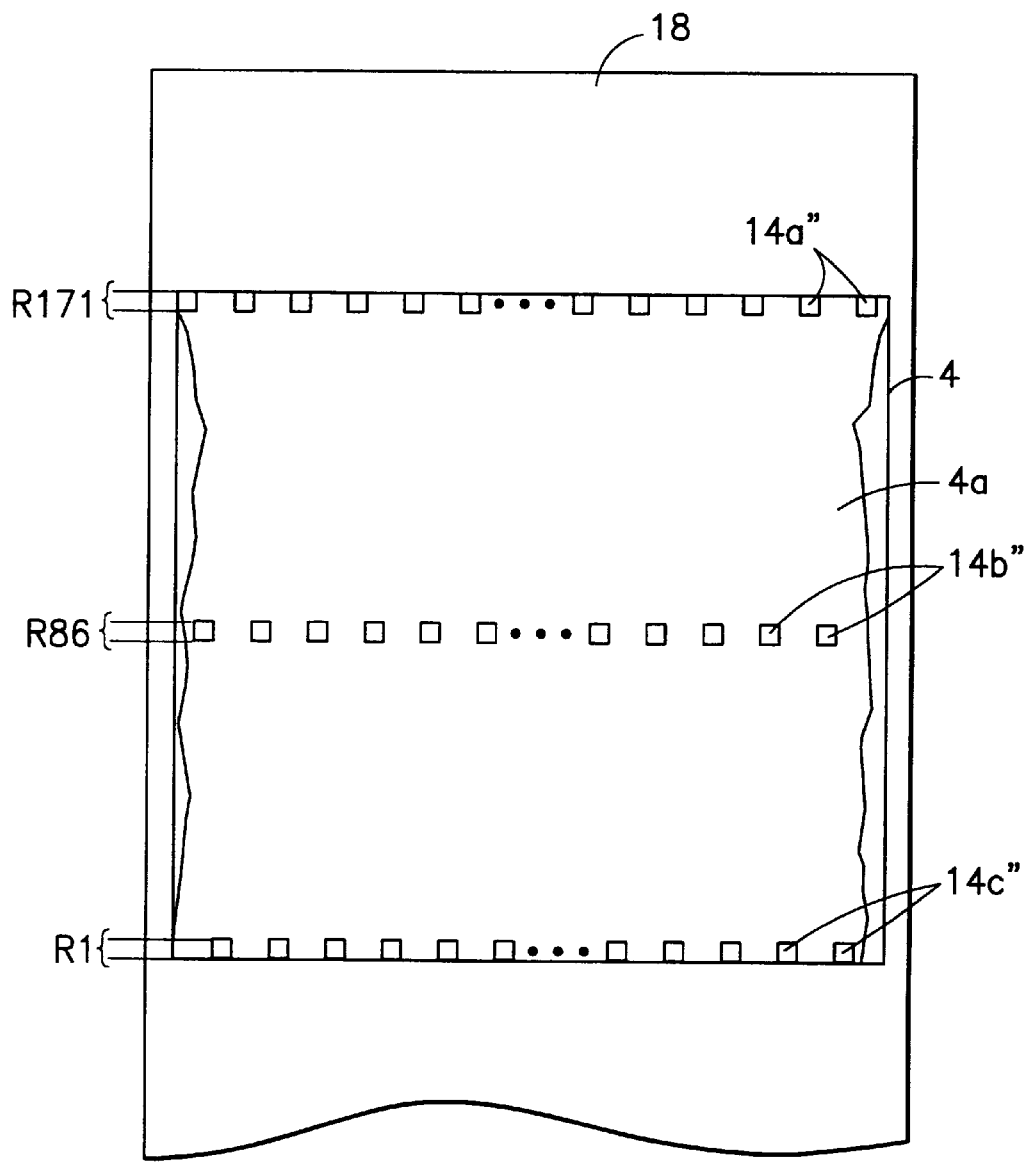

After the sample slide 4 has been advanced through step 170, and assuming that as a step 171 the slide 4 is again advanced at block B by distance (W1) (so that edge 4a' reaches location P171) and another pulse beam is fired from source illuminator 3 at block C, the sample slide 4 becomes illuminated by all three slit image groups 14a", 14b", and 14c", as may be understood in view of FIGS. 9d, 9j, and 10d, wherein FIG. 9j shows a perspective view of the sample slide 4 and a portion of the mask 14. In particular, for step 171 rows R1, R86, and R171 become illuminated by slit images from slit image groups 14c", 14b", and 14a", respectively, as a result of the pulse beam being fired at block C (see FIG. 10d). Any fluorescent emissions that occur as a result of the markers 40a–40c being illuminated by these slit image groups 14a", 14b", and 14c" are detected at block D, and the steps indicated by blocks E-I' are then performed in a similar manner as was described above.

For each of the step numbers from 172 through 256, the pulse beam firing at block C causes the sample slide 4 to be illuminated by the slit image groups 14a", 14b", and 14c". Any marker fluorescent emissions that occur as a result of the markers 40a–40c being illuminated by these slit image groups 14a"–14c" are detected at block D, the steps indicated by blocks E-I'0 are performed in a similar manner as was described above. Assuming that the amplitude of at least one of the signals output by the detector array 25 during each individual one of these steps is determined to be greater than the predetermined threshold level at block E, then the value of variable STEP identifying the step number is stored in memory 31 at block G.

Figure 10E:
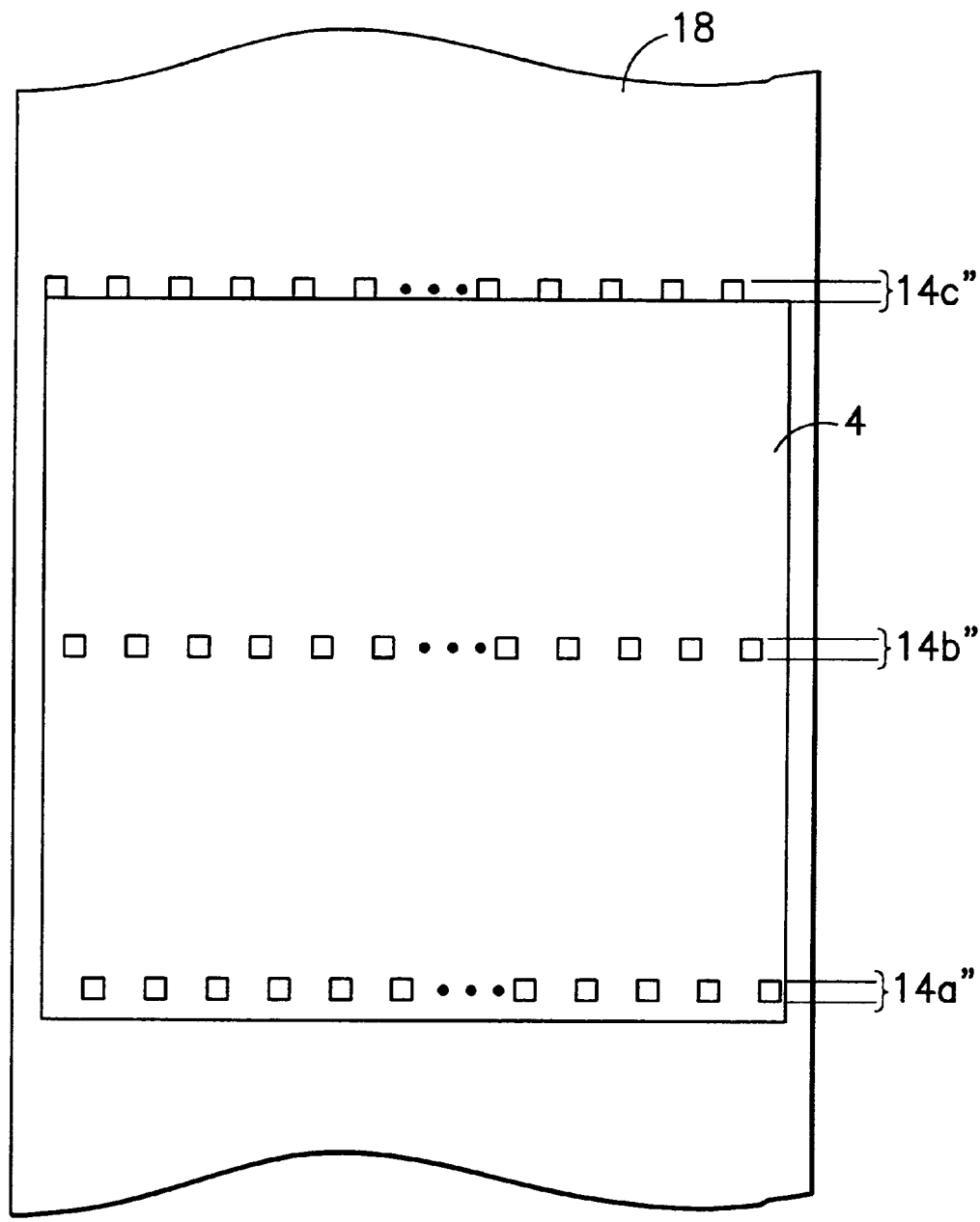

After the sample slide 4 has been advanced through step 256, and assuming that as a step 257 the sample slide 4 is again advanced at block B by distance (W1) and another pulse beam is fired from source illuminator 3 at block C, the pulse beam causes the sample slide 4 to be illuminated by slits from slit image groups 14b" and 14c" only. This can be appreciated in view of FIGS. 9e and 10e. For each advancement of the slide 4 through steps 257 through 341, any marker emissions that occur as a result of the markers 40a–40c being illuminated by these slit image groups 14b" and 14c" are detected at block D, and, assuming that the amplitudes of at least one of the signals output by the detector array 25 exceeds the predetermined threshold level, the value of STEP indicating the step number is stored in memory 31 in a similar manner as was described above. Any detections resulting from the other slit image group 14a" illuminating the surface 18' of the stage 18 are ignored by the control processor 30, as was described above.

Figure 9K:
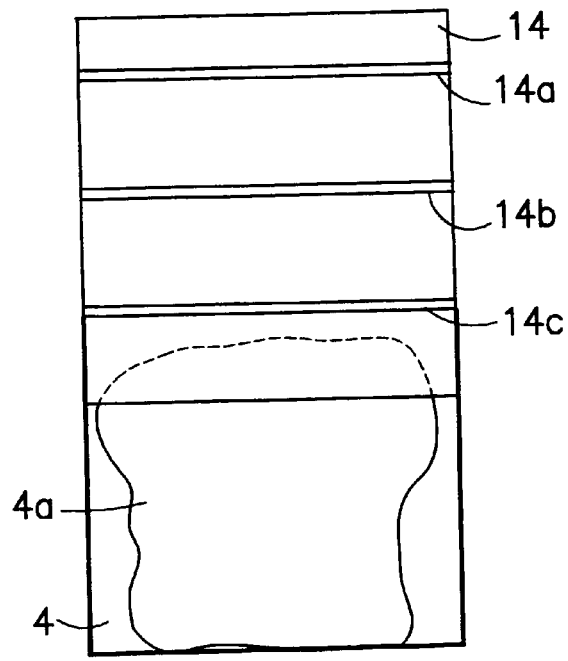
Figure 10F:
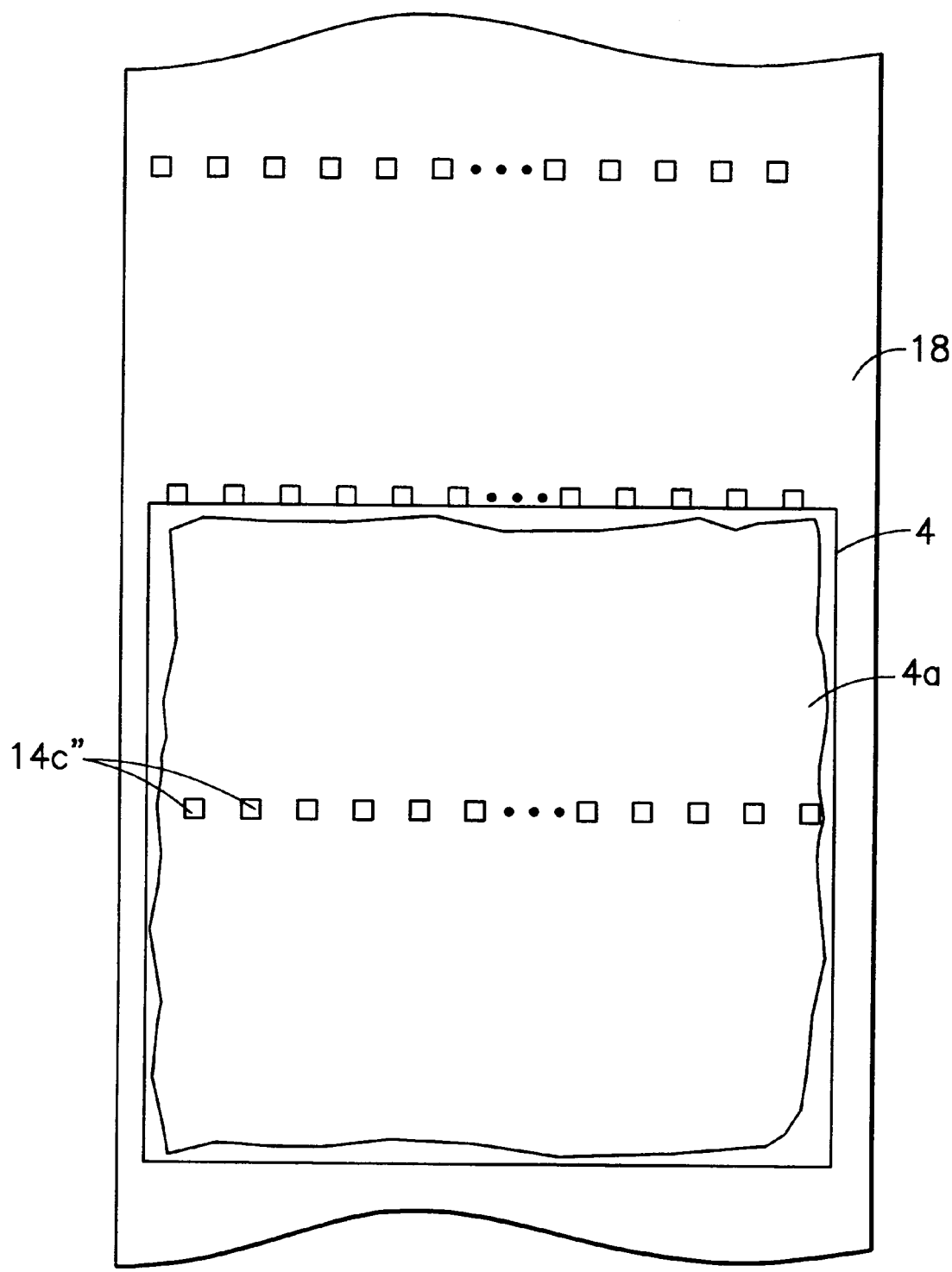
Figure 10G:
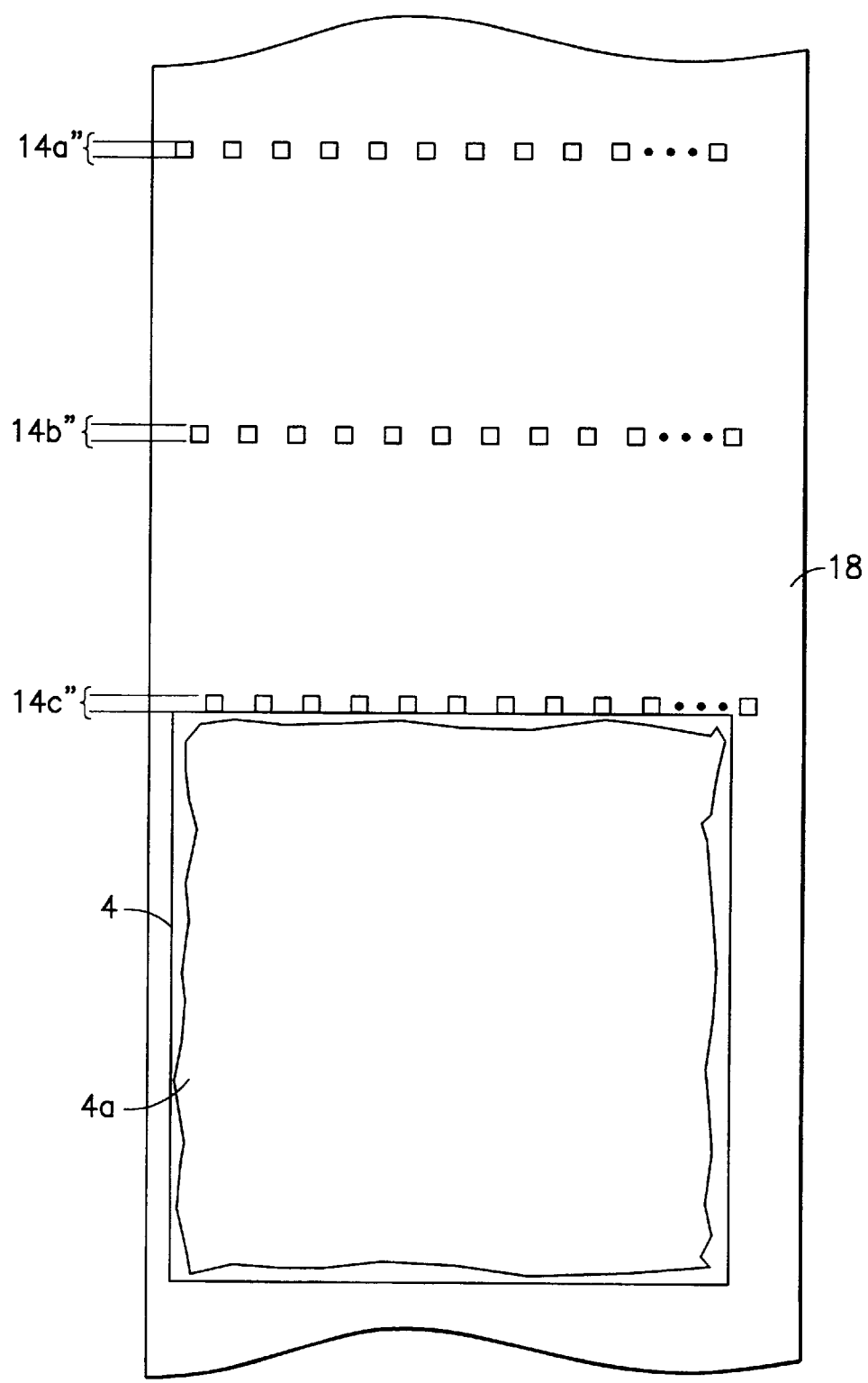

For advancements of the slide 4 from step numbers 342 through 426 (and assuming that the source illuminator 3 fires a pulse beam at block C for each step number), the sample slide 4 is illuminated by slit image beams group 14c' (and corresponding slit image group 14c") only. This can be appreciated in view of FIGS. 9f, 9k, and 10f which show the sample slide 4 in a position corresponding to step number 342. For step numbers 342–426, any marker fluorescent emissions that occur as a result of the markers 40a–40c being illuminated by slit image group 14c" are detected at block D, and, assuming that the amplitudes of at least one of the signals output by the detector array 25 exceeds the predetermined threshold level, the value of STEP indicating the step number is stored in memory 31 in a similar manner as was described above. Any detections resulting from the other slit image groups 14a" and 14b" illuminating the surface 18' of the stage 18 are ignored by the control processor 30, in the manner described above.

Reference will now be made to the case where at block I' it is determined that the value of variable STEP exceeds 426. Upon the control processor 30 determining that the value of variable STEP is greater than 426 at block I' ('Yes' at block I'), control passes to block J where the control processor 30 examines the memory 31 to determine whether or not any information was previously stored therein at block G for any of the respective steps 1 to 426. If the control processor 30 determines that information (i.e., values of variable STEP) was stored in memory 31 for any of the step numbers 1 to 426 (indicated by 'Y' at block K), then control passes to block K1 where the control processor 30 controls the stage 18 so as to reposition the sample slide 4 to the position depicted in FIGS. 9a and 10a (where the front edge 4a' of the slide 4 is parallel to the axis y'). Control then passes through connector 3 to block M (FIG. 5a), where further procedures are performed in a manner as will be described below.

If at block K the control processor 30 determines that no information was previously stored in the memory 31 for any of the step numbers 1 to 426 (indicating that none of the proteins being tested for are present within the sample 4a) ('N' at block K), then control passes to block L', where additional types of fluorescent markers may be added to the sample 4a, if it is desired to further test the sample 4 for the presence of other types of proteins.

If it is not desired to examine the sample 4a for the presence of other types of proteins, and no additional markers are added to the sample 4a ('N' at block L'), then the procedure is terminated at block L2.

If it is desired to examine the sample 4a for the presence of other proteins ('Y' at block L'), then the additional markers are added to the sample 4a at block L1'. The number and types of markers added to the sample 4a at block L1' many be any selected number and types of markers, although preferably only up to a total of 22 additional markers are added, since, as is known in the art, where more than a total of 25 markers are included in a sample, fluorescent radiation produced by one or more of the markers may excite other ones of the markers. For the purposes of this description, it is assumed that it is desired to examine the sample 4 for the presence of various types of proteins, that 22 of the markers from the list shown in FIGS. 3a and 3b are added to the sample 4 at block L1', and that these markers are different than the markers 40a–40c previously included in the sample 4.

After the additional markers are added to the sample 4a at block L1', control passes through connector 3a back to block A where the initial screening mode procedures of FIGS. 4a and 4b are again performed to determine whether any of the proteins being tested for are present in the sample 4a. These procedures are performed in a similar manner as described above and thus will not be described in further detail, although it should be noted that because the sample 4a now includes the additional markers added to the sample 4 at block L1', the wavelengths employed for illuminating the sample 4a include those which are known to "excite" these additional markers (i.e., the pulse beam fired from the source illuminator 3 at block C includes wavelengths for "exciting" the additional markers).

In view of the foregoing description, it can be appreciated that the procedures of the "initial screening mode" enable a determination to be made of whether or not proteins (and hence, cancerous cells) are included in the sample 4a. After a determination is made that there are proteins included in the sample 4a (indicated by 'Y' at block K), the procedures of the "high resolution operating mode" are performed in order to enable the specific types of proteins included in the sample 4a to be identified. The procedures of the "high resolution operating mode" will now be described.

Figure 5A:
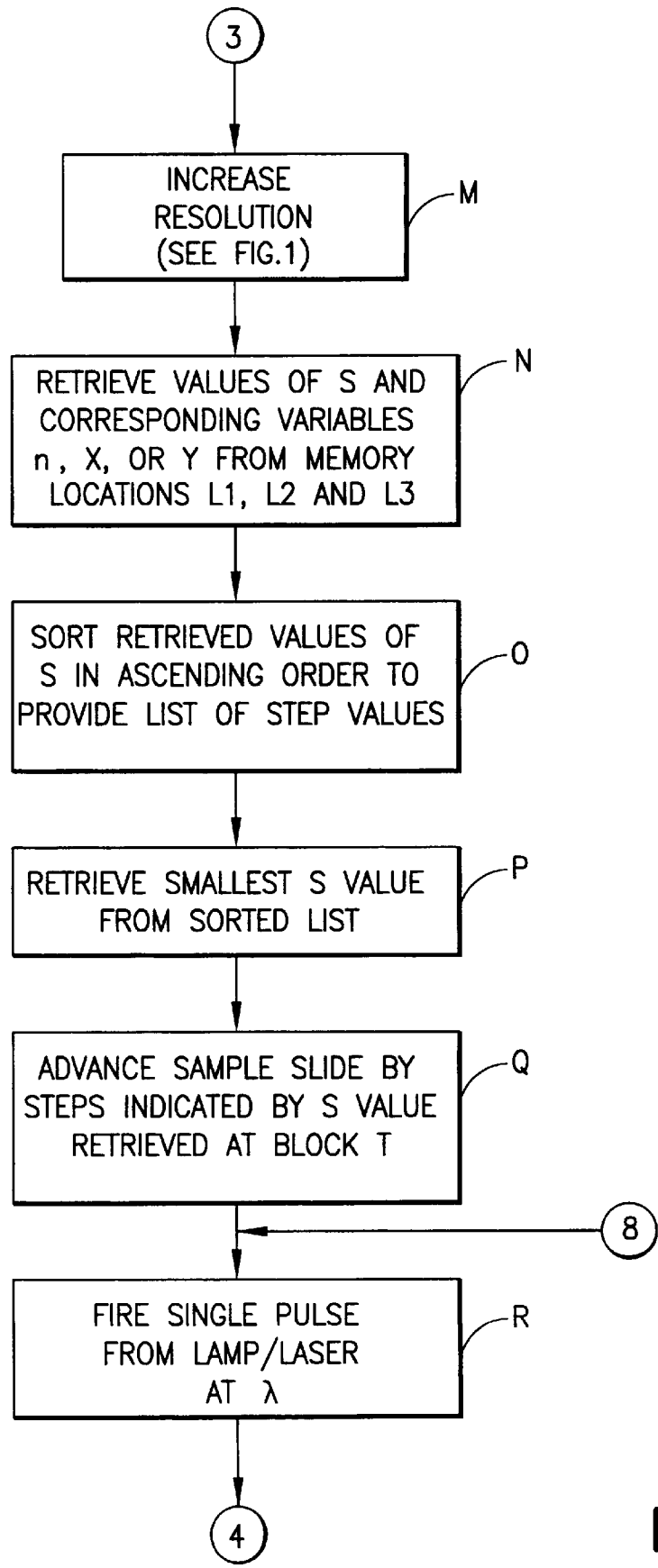
FIGS. 5a–5d show a flow diagram depicting another portion of the method of this invention.
Figure 5B:
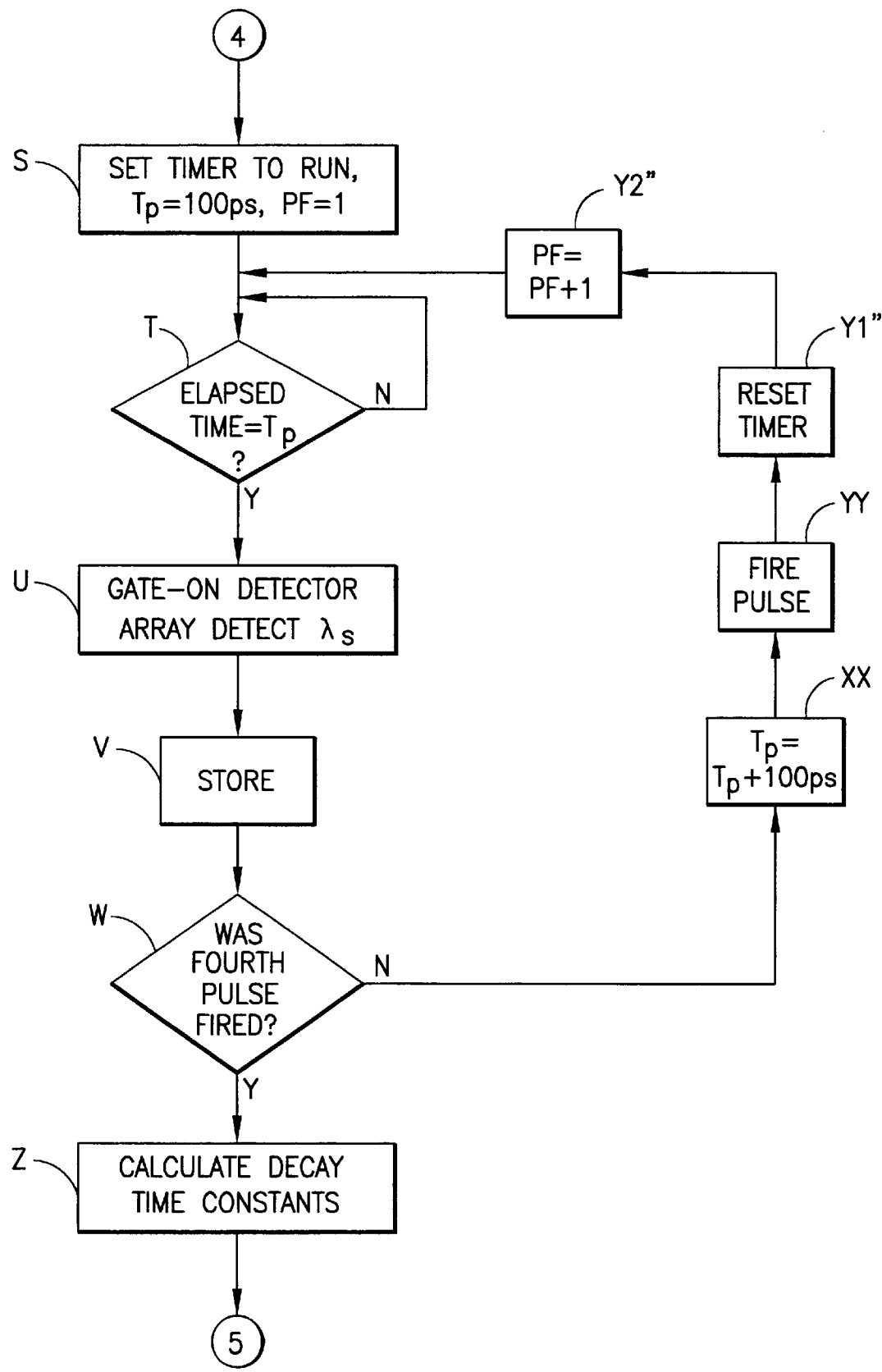

As was described above, if the control processor 30 determines at block K that information was stored in memory 31 for any of the step numbers 1 to 426 (indicating that one or more proteins are present in the sample 4a), then control passes to block K1 where the stage 18 is again controlled so as to reposition the sample slide 4 to the position depicted by FIGS. 9a and 10a. Thereafter, control passes through connector 3 to block M (FIG. 5a). At block M, if desired, the objective 16 may be replaced with another objective that provides a greater magnification level (e.g., a 1:15 magnification ratio) than the one employed during the initial screening mode, to enable greater resolution to be provided for images detected by detector array 25. For the purposes of this description, it is assumed that the objective 16 is replaced at block M with another objective having an increased magnification level.

After block M, control passes to block N where the control processor 30 retrieves the value(s) of variable STEP that were previously stored in memory 31 at block G. Thereafter, at block C the control processor 30 performs an algorithm for sorting the values retrieved at block N in ascending order to provide a list of step values. The sorting algorithm employed by the control processor 30 may be any suitable type of algorithm known in the art for sorting values in ascending order.

At block P the control processor 30 retrieves a smallest one of the values from the list of values sorted at block O, and then at block Q the control processor 30 controls the stage 18 so as to advance the sample slide 4 by the number of steps indicated by the value retrieved at block P (i.e., by a distance that is equal to the product of the width (W1)×the value retrieved at block P) in order to position the slide 4 at a location on the stage 18 corresponding to the value retrieved at block P. In this manner, a first portion of the sample 4a previously determined to include one or more proteins during the initial screening mode may be examined to identify the specific type(s) of the protein(s) included in this portion of the sample 4a.

After block Q, control is passed to block R where the control processor 30 controls the source illuminator 3 so as to cause the source illuminator 3 to fire a single pulse beam of selected wavelengths. By example, assuming that only three markers are included in the sample, then the pulse beam fired at block R includes three corresponding wavelengths that are known to cause the respective markers to fluoresce. Also by example, and assuming that 22 markers were previously added to the sample 4a at block L1', then the pulse beam fired at block R includes 22 corresponding wavelengths that are known to cause respective ones of the markers to fluoresce and emit a characteristic radiation wavelength.

At block S the control processor 30 sets timer 30b (of control processor 30) to run beginning at a time when the pulse beam fired by source illuminator 3 at block R ends, and variable PF is set equal to "1". Thereafter, upon the control processor 30 determining that the timer 30b reaches the first predetermined time period value specified by variable $T_P$ stored in memory 31 ('Y' at block T), control passes to block U. At block U the control processor 30 signals the detector array 25 so as to enable the gate array 25c of the detector array 25 for a second predetermined time period (also referred to as a "sampling period") beginning at a time when the first predetermined time period ends. As a result, the detector array 25 outputs to control processor 30 signals corresponding to any wavelengths detected by the detector array 25 while the gate array 25c is enabled. As was previously described, the signals output by the detector array 25 represent image information detected by the detector array 25.

Figure 11A:
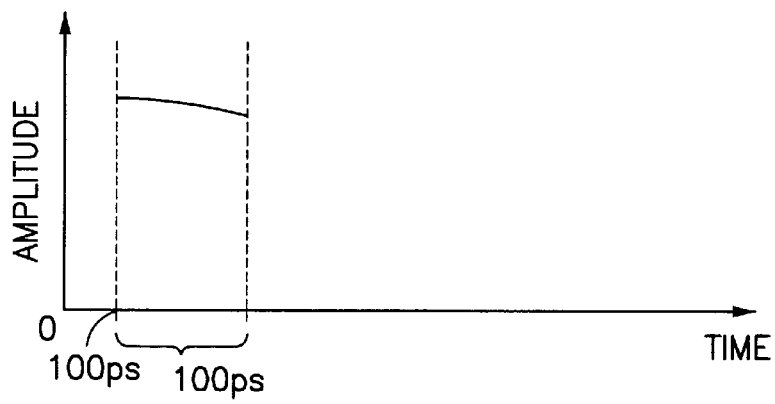
FIGS. 11a–11d show exemplary curves of a signal that corresponds to emission wavelengths detected by the detector array of FIG. 8 during various sampling periods.

Preferably, the first predetermined time period value specified by the variable $T_P$ and the sampling period are such that peak amplitudes of any wavelengths emitted from sample 4a in response to the pulse beam being fired at block R can be detected by the detector array 25 (taking into account characteristic "lifetimes" or decay times of the marker emissions), and corresponding signals can be output from the detector array 25 during the sampling period. By example, and in accordance with a preferred embodiment of the invention, the first predetermined time period value equals approximately 100 ps, and, assuming that the minimum decay time of a marker emission is approximately 1 ns, then the duration of the "sampling period" is also 100 ps. Also by example, and assuming that the minimum decay time of a marker emission is approximately 4 ns, then the duration of the "sampling period" is preferably 500 ps. An exemplary curve representing a portion of a signal corresponding to a marker emission wavelength detected during the sampling period at block U is shown in FIG. 11a.

After the detector array 25 outputs the information signals to the control processor 30 at block U on a row-by-row basis, the signals are A/D converted and the amplitudes of the signals are compared to the predetermined threshold level in the manner described above. Those signals having amplitudes which are determined to not exceed the predetermined threshold level are ignored by the control processor 30, and those signals having amplitudes which are determined to exceed the predetermined threshold level are stored in respective storage bins 70 of the frame store F1 (block V). That is, for each respective one of the signals that is determined to have an amplitude exceeding the predetermined threshold level, the signal is stored in a particular storage bin 70 within frame store F1 corresponding to the radiation detector element which detected the wavelength corresponding to the signal. Thereafter, being that the value of variable PF is equal to "1", indicating that only a single pulse beam has been fired from the source illuminator 3 during the high resolution mode ('N' at block W), control passes to block XX where the value stored as variable $T_P$ is retrieved and incremented by a predetermined amount to provide a first updated value. The first updated value is then stored as the variable $T_P$. By example, and in accordance with a preferred embodiment of the invention, the value of variable $T_P$ is incremented at block XX by an amount equal to the value of the first predetermined time period (i.e., approximately 100 ps), and the first updated value equals 200.

Figure 11B:
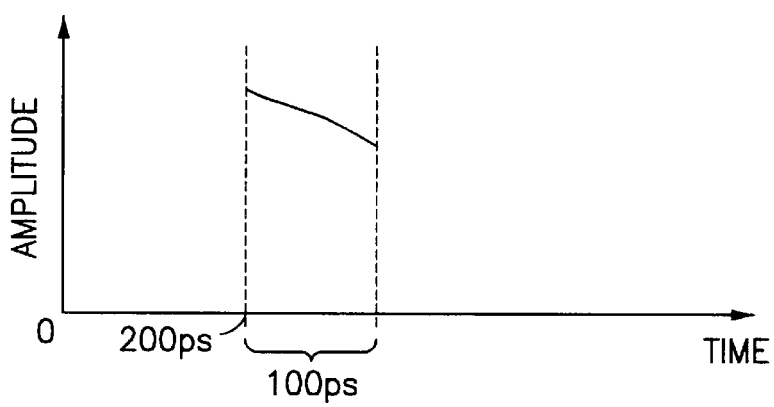

Control then passes to block YY where the control processor 30 again controls the source illuminator 3 so as to cause the source illuminator 3 to fire another pulse beam for illuminating the sample 4a. Then, the timer 30b is reset beginning at a time when the firing of the pulse beam ends (block Y1"), the value of variable PF is incremented by "1". Thereafter, the steps designated by blocks T–W are performed again in a similar manner as was described above, except that at block U the gate array 25c of detector array 25 is enabled for the duration of the "sampling period" (e.g., at least 100 ps) in response to the timer 30b reaching (at block T) the first updated value obtained previously at block XX. Also, for each respective one of the signals that is output by the detector array 25 at block U, and which is determined to have an amplitude exceeding the predetermined threshold level, the signal is stored in a particular storage bin 70 within frame store F2 corresponding to the radiation detector element which detected the wavelength corresponding to the signal (block V). An exemplary portion of a curve representing one of these signals is shown in FIG. 11b.

Figure 11C:
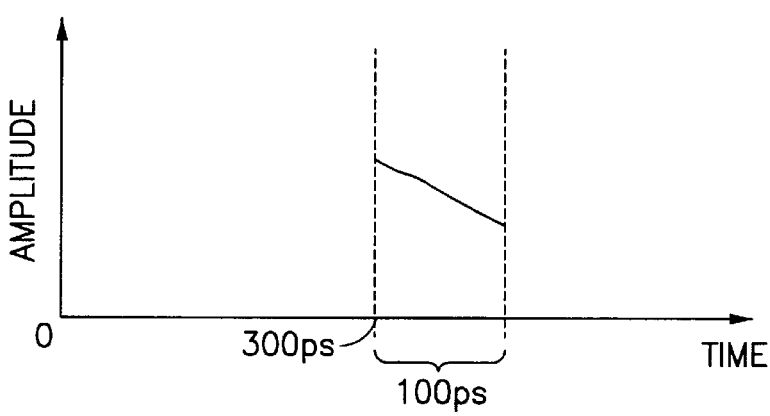

After the signals are stored at block V as a result of the previous firing of the pulse beam, and being that the value of variable PF is now equal to "2" (indicating that only two pulse beams have been fired during the high resolution operating mode; i.e., 'n' at block W), control passes via block W to block XX. At block XX the value most recently stored as variable $T_P$ (i.e., the first updated value) is retrieved and incremented by an amount equal to the predetermined time period value (e.g., 100 ps) to provide a second updated value (e.g., 300 ps). The second updated value is then stored as the variable $T_P$. Then, the timer 30b is again reset beginning at a time when the firing of the pulse beam ends (block Y1"), and the procedures designated by blocks Y2"–W are performed in a similar manner as was described above, except that at block U the gate array 25c of detector array 25 is enabled in response to the timer 30b reaching (at block T) the second updated value (e.g., 300 ps) specified at block XX. Also, for each respective one of the signals that is output by the detector array 25 at block U, and which is determined to have an amplitude exceeding the predetermined threshold level, the signal is stored in a particular storage bin 70 within frame store F3 corresponding to the radiation detector element which detected the wavelength corresponding to the signal (block V). An exemplary portion of a curve representing one of these signals is shown in FIG. 11c.

Figure 11D:
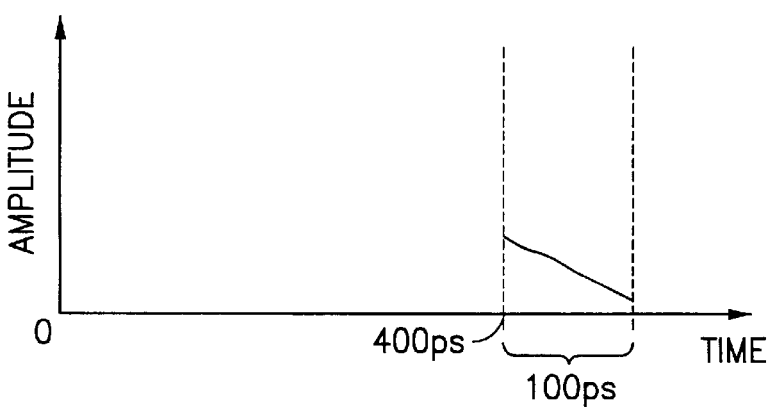

After the signals are stored at block V, and assuming that the value of PF is now equal to three (indicating that three pulse beams have been fired during the high resolution operating mode; i.e., 'n' at block W), control again passes via block W to block XX. At block XX the most recently stored value of variable $T_P$ (i.e., the second updated value) is retrieved and incremented by an amount equal to the first predetermined time period value (e.g., 100 ps) to provide a third updated value (e.g., 400 ps). The third updated value is then stored as the variable $T_P$. At block YY the control processor 30 again controls the source illuminator 3 so as to cause the source illuminator 3 to fire another (i.e., fourth) pulse beam. At block Y1" the timer 30b is again reset beginning from the time when the firing of the pulse beam at block YY ends, and then at block Y2" the value of PF is increased by "1" to value "4". Upon the control processor 30 determining that the timer 30b reaches the third updated value (e.g., 400 ps), the control processor 30 again enables the gate array 25c of detector array 25. For each respective one of the signals that is output by detector array 25 at block U and which is determined to have an amplitude exceeding the predetermined threshold level, the signal is stored in a particular storage bin 70 within frame store F4 corresponding to the radiation detector element which detected the wavelength corresponding to the signal (block V). An exemplary curve representing a portion of one of these signals is shown in FIG. 11d.

Figure 15:
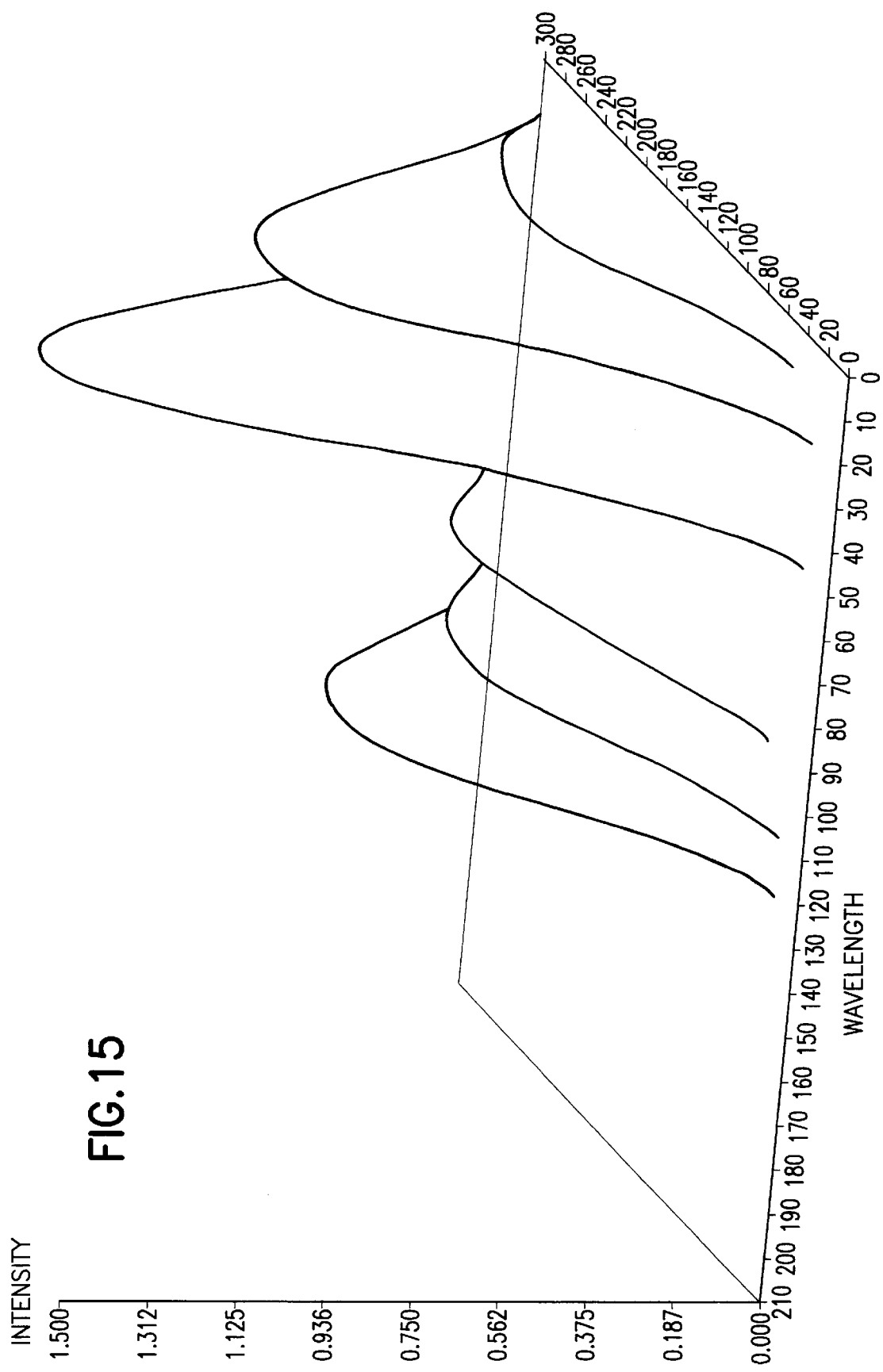
FIG. 15 shows exemplary marker emission response profiles.

As another example, FIG. 15 shows exemplary emission response profiles of various types of markers, as detected by the detector array 25 over the sampling periods, compositely.

After the control processor 30 determines that the value of variable PF is equal to "4", indicating that a fourth pulse beam has been fired during the high resolution operating mode ('y' at block W), then control passes to block Z. At block Z the control processor 30 retrieves the signals from corresponding ones of the storage bins 70 of the respective frame stores F1–F4, and performs a predefined algorithm using the retrieved signals to calculate respective decay time constants. By example, and referring to FIGS. 11a–11d and 14b, assuming that 1) first storage bin 70a of frame store F1 stores a signal having a curve similar to that shown in FIG. 11a, 2) storage bin 70b of frame store F2 stores a signal having a curve similar to that shown in FIG. 11b, 3) storage bin 70c of frame store F3 stores a signal having a curve similar to that of FIG. 11c, and 4) storage bin 70d of frame store F4 stores a signal having a curve similar to that of FIG.

11d, then the control processor 30 retrieves these signals and employs them in the predefined algorithm to calculate a decay time constant based upon these signals. A similar procedure is carried out by the control processor 30 to determine decay time constants for signals stored in other, corresponding ones of the storage bins 70 of the respective frame stores F1–F4. The decay time constants calculated for the signals from corresponding ones of the storage bins 70 of the respective frame stores F1–F4 are stored in respective ones of storage bins 74 of the table T2. By example, a decay time (TC) constant value which is calculated based on the information retrieved from storage bins 70a–70d of the respective frame stores F1–F4 is stored in storage bin 74d of table T2.

It should be noted that the predefined algorithm may be any suitable known type of algorithm for calculating decay time constants based on signal information.

Figure 5C:
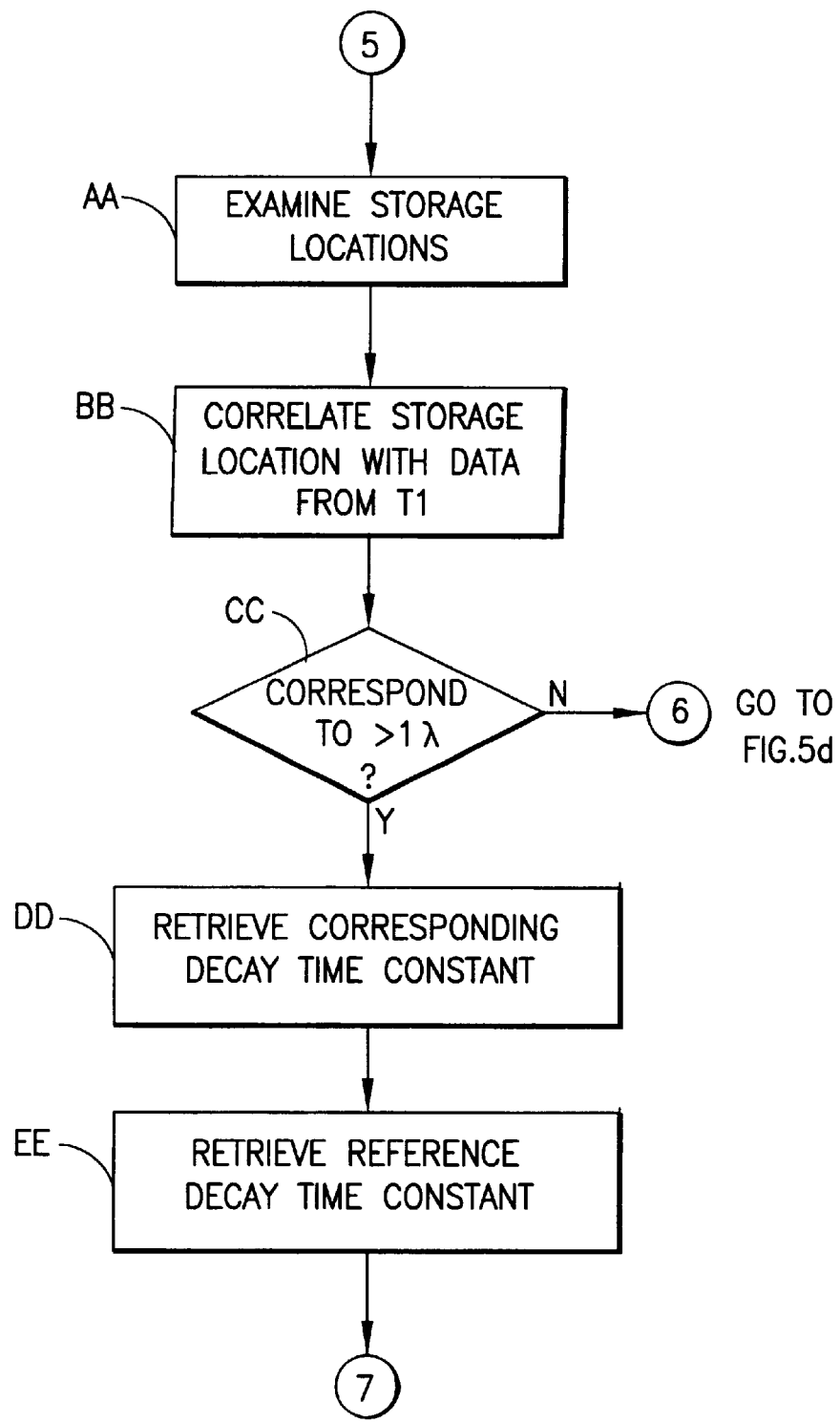

After the decay time constants are calculated at block Z, control then passes through connector 5 to block AA of FIG. 5c where procedures in accordance with the spectral analysis mode of the invention are performed. In accordance with the spectral analysis mode, at block AA the control processor 30 examines the storage bins 70 of the frame store F1 to determine which ones of the rows 71a–71n of storage bins 70 have signals stored therein (i.e., these signals were stored previously at block V). As was previously described, (and as is known by the control processor 30) each one of the rows 71a–71n of storage bins 70 corresponds to a particular band of wavelengths, in that each row 71a–71n of storage bins 70 stores signals having wavelengths within a particular band of wavelengths detected by respective rows of radiation detector elements of the detector array 25 (for convenience, it may simply be assumed that each row 71a–71n corresponds to a particular wavelength emitted by the markers 40 included in the sample 4a). Each of the rows 71a–71n of storage bins 70 also corresponds to one or more reference marker emission wavelength values (that are within the band of wavelengths to which the row corresponds), and also to corresponding markers located within same rows (see FIGS. 3a and 3b) of table T1 as these reference emission wavelength values. As such, for those rows 71a–71n of storage bins 70 that are determined to include signals, the control processor 30 correlates these rows 71a–71n of storage bins 70 (and hence the storage bins and the wavelength of the signals stored in these storage bins) to the corresponding one or more reference marker emission wavelength values from table T1 (block BB). By example, the assuming that the control processor 30 has knowledge that row 71a corresponds to a wavelength of 405 nm, the step of correlating may be performed by the control processor 30 comparing the value of 405 nm to the reference emission wavelength values from Table T1, in order to find matching reference emission wavelength value(s) in this table. For this example, it can be seen in view of FIG. 3a that marker INDO1 has a matching reference emission wavelength value of 405 nm.

For cases in which the control processor 30 determines that respective ones of these rows 71a–71n of storage bins 70 (and hence respective ones of the wavelengths of the signals stored in these bins) correlate to a reference emission wavelength value of only a single type of marker in table T1 ('n' at block CC), then control passes through connector 6 to block HH where the control processor 30 retrieves the information identifying the name of the marker associated with the wavelength value from table T1 and displays the name of the marker on the display 32. By example, in the example described above, after determining that row 71a corresponds to the reference emission wavelength value of 405 nm from table T1 (see column 3 of FIG. 3a), the control processor 30 retrieves associated information specifying "INDO1" from the table T1 and presents this information on the display 32. An operator may then associate the presented marker name with an associated protein to determine which type of protein, and hence, which corresponding type of cancerous cells, are present in the sample 4a.

It should be noted that in accordance with other embodiments of the invention, other information is also presented on the display 32. By example, and as was described above, in addition to information specifying marker names, the table T1 also preferably stores information specifying protein identifier names that correspond to the marker names. In accordance with another embodiment, the table T1 may also store information specifying identifier names for particular types of cancer cells which produce respective ones of these proteins. As such, in one embodiment, for cases in which the control processor 30 determines that respective ones of these rows 71a–71n of storage bins 70 correlate to a reference emission wavelength value of only a single type of marker in table T1 ('n' at block CC), then at block HH the control processor 30 may retrieve the information specifying the name of the protein and/or cancer cell associated with the reference emission wavelength value, and then control the display 32 so as to present this information on the display 32.

For respective ones of the rows 71a–71n of storage bins 70 that are determined to correspond to a reference emission wavelength value of more than a single type of marker from table T1 ('y' at block CC), a temporal analysis is performed to determine which one(s) of the markers the rows 71a–71n of storage bins 70 correspond to. By example, one of the rows 71a–71n of storage bins 70 may be determined at block CC to correspond to a value 533 nm from table T1. As can be seen in FIGS. 3a and 3b, the value 533 nm appears more than once in FIGS. 3a and 3b, and thus is the peak emission wavelength value of more than a single marker, such as markers Calcium Green and Toto-1. In this case, the performance of block CC results in control passing to block DD where the temporal analysis is initiated to resolve which one(s) of the markers emitted fluorescent radiation in response to being illuminated by slit images. It should be noted that the step of block CC may be performed by using any suitable table processing techniques.

In accordance with the temporal analysis, the control processor 30 compares reference fluorescence decay time constant values from the table T1 to calculated fluorescence decay time constant values corresponding to storage bins 70 of those rows 71a–71n determined at block CC to correspond to more than one marker from table T1. As was previously described, the reference decay time constant values define known decay time constant values of the various types of markers employed in the sample 4a. An example of a number of reference time constant values associated with various types of markers (and stored in table T1) is shown in column 5 of FIGS. 3a and 3b. By comparing the calculated decay time constant values to the reference decay time constant values corresponding to the storage bins 70, it can be determined which one(s) of the markers correspond to these storage bins 70, and hence, which one(s) of the markers emitted fluorescent radiation in response to being illuminated by slit images.

Accordingly, it can also be determined that one or more particular types of proteins are present in the sample 4a, indicating that corresponding type(s) of cancerous cells are also included in the sample 4a.

Referring again to FIG. 5c, the temporal analysis will now be described in further detail. At block DD the control processor 30 retrieves each decay time constant value which corresponds to respective storage bins 70 of those rows 71a–71n determined at block CC to correspond to a reference emission wavelength value of more than a single type of marker (from table T1). Each decay time constant value is retrieved from storage bins 74 (of table T2) corresponding to the respective storage bins 70 of these rows 71a–71n. By example, assuming that at block CC it was determined that row 71a corresponds to a reference emission wavelength value of more than a single type of marker from table T1, then at block DD the decay time constant values from a row 74b of storage bins 74 (of table T2) corresponding to row 71a are retrieved.

After block DD is performed, control passes to block EE. At block EE the control processor 30 retrieves the reference decay time constant values corresponding to the reference emission wavelengths that correspond to the rows 71a–71n determined at block CC to correspond to more than a single type of marker. By example, for the example above the control processor 30 retrieves from table T1 the reference decay time constant value corresponding to the reference emission wavelength to which row 71a corresponds. As was previously described, an example of at least some of the reference decay time constants stored in the table T1 are shown in column 5 of FIGS. 3a and 3b, and an example of the reference emission wavelength values (from table T1) which correspond to these reference decay time constants are shown in column 1 of FIGS. 3a and 3b.

Figure 5D:
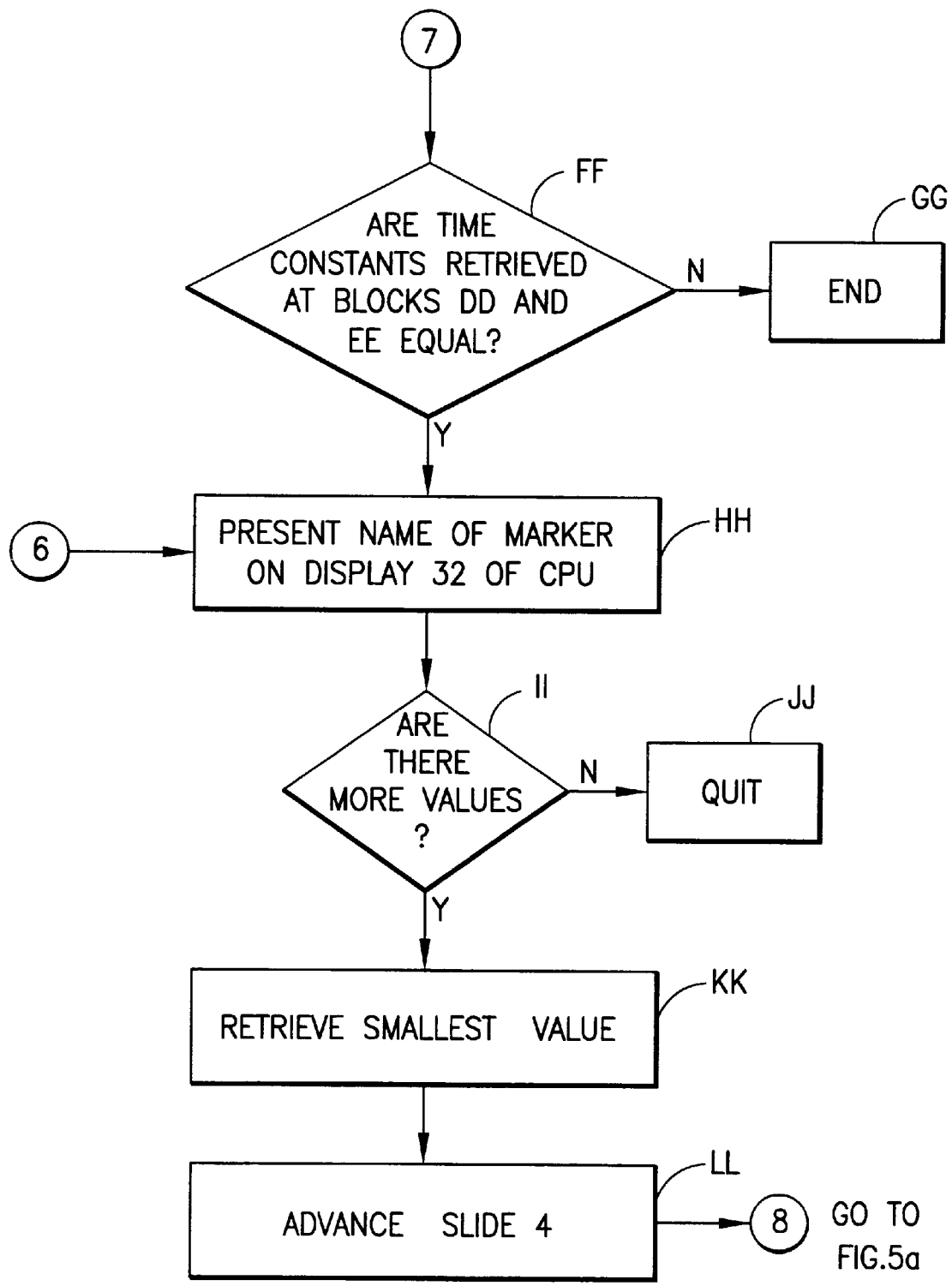

Thereafter, control passes through connector 7 to block FF of FIG. 5d. At block FF the control processor 30 compares each value retrieved at block DD to each of the respective values retrieved at block EE to determine whether or not the values retrieved at block DD are within a predetermined range of the respective values retrieved at block EE. In accordance with one embodiment of the invention the step of block FF is performed so as to determine whether any of the respective values retrieved at block DD are within +10% of the respective values retrieved at block EE.

If 'no' at block FF, then no information is presented in the display 32 and control passes to block GG where the method is terminated. By example, assuming that the values retrieved at block DD are 1ns and 1.7 ns, and that at block EE reference decay time constant values of 2.4 ns and 3.4 ns are retrieved, then the performance of the step of block FF results in control passing to block GG.

If it is determined at block FF that a respective decay time constant value retrieved previously at block DD is within the predetermined range of one of the reference decay time constant values retrieved previously at block EE ('y' at block FF), then control passes to block HH where the control processor 30 retrieves the information specifying the name of the marker associated with this reference decay time constant value and controls the display 32 so as to present the name of the marker on the display 32. An operator may then associate the presented maker name with an associated protein to determine which type of protein, and hence, which corresponding type of cancerous cell, are present in the sample 4a. By example, assuming that the decay time constant values retrieved previously at block DD are 1ns and 1.7 ns, and that at block EE reference decay time constant values of 1ns and 1.7 ns are retrieved, then the performance of the step of block FF results in control passing to block HH where the names of the markers associated with these respective decay time constant values are presented on the display 32. Also by example, and assuming that the decay time constant values retrieved previously at block DD are 1ns and 1.7 ns, and that at block EE reference decay time constant values of 2.7 ns and 1.7 ns are retrieved, then the performance of the step of block FF results in control passing to block HH where only the name of the marker (e.g., TOTO-1) corresponding to the value 1.7 ns is presented on the display 32.

It should be noted that the step designated by block HH may also be performed in accordance with other suitable embodiments. By example, and as was described above, in addition to information specifying reference decay time constant values and marker name identifiers, the table Ti also preferably stores information specifying protein identifier names that correspond to the marker names. In accordance with another embodiment, the table T1 may also store information specifying identifier names for particular types of cancer cells which produce respective ones of these proteins. As such, after it is determined at block FF that one of the decay time constant values retrieved at block DD is within the predetermined range of a reference decay time constant value retrieved at block EE, then at block HH the control processor 30 may retrieve the information specifying one or more of these identifier names associated with the reference decay time constant value, and then control the display 32 so as to present one or more of these identifier names on the display 32.

After the step identified by block HH is performed, then at block II the control processor 30 determines whether or not there are any additional step number values (i.e., values of variable STEP) to be retrieved from the sorted list obtained previously at block 0. If 'yes, at block II then the control processor 30 retrieves a next smallest one of these values from the list at block KK. Thereafter, at block LL the control processor 30 controls the stage 18 to advance the sample slide 4 so that the edge 4a' of the slide reaches a position corresponding to the retrieved step number value. Control then passes through connector 8 back to block R of FIG. 5a, where the method continues in the manner described above.

If 'no' at block II (indicating that there are no more values to be retrieved from the list sorted previously at block 0), then control passes to block JJ where the method is terminated.

Another aspect of this invention will now be described. As was previously described, during the initial screening mode, after the sample 4a has been completely "screened", the memory 31 is examined at block J to determine whether or not values of variable STEP were previously stored therein, indicating that marker emission wavelengths have been detected by detector array 25 and, hence, that one or more proteins and corresponding cancer cells are included in the sample 4a (block K). As was also previously described, the markers 40 included in the sample 4a typically substantially cover the area of the corresponding cancer cells (i.e., the area visible to the imaging system). As such, by detecting the emission wavelengths (i.e., image) of these markers, a shape and size of the cancer cells can be determined. According to this aspect of the invention, after the sample slide 4 has been advanced through all of the 426 "steps" and it is determined that one or more proteins are included in the sample 4a (and prior to block K1), the control processor 30 performs a procedure for determining the approximate size (e.g., area) and shape of the cancer cells. By example, the control processor 30 examines the frame store F1 to determine the number of storage bins of the frame store F1 which have signals stored therein (as a result of the performance of the initial screening mode procedures). Assuming that the control processor 30 knows the surface area (e.g., approximately 5 to 10 microns) of each one of the radiation detector elements of the detector array 25, the control processor performs an algorithm for determining an approximate area of the cancer cells. By example, the control processor 30 may perform the algorithm by multiplying the known value of an individual radiation detector element surface area by the number of storage bins 70 determined to be storing signals to calculate a value representing the approximate area of the cancer cells.

Thereafter, the control processor 30 controls the display 32 so as to present the calculated value to the operator of the imaging system 11. The control processor 30 may also retrieve the signals from the storage bins (i.e., retrieve the stored, detected image) and present the image on the display 32 so that the shape of the cancer cell(s) included in the sample 4a can be viewed by the operator. This step may be done using a suitable scaling factor so that the image is scaled appropriately.

Also in accordance with this invention, information representing images of known types of cancer cells may be stored in the table T1 in association with the corresponding protein and marker information. In accordance with this aspect of the invention the image(s) detected by the detector array 25 are compared to the image information stored in the table T1 to determine whether or not the compared images are substantially similar to one another. This step may be performed using any suitable optical correlation technique. If it is determined that the compared images are substantially similar to one another, then the control processor 30 retrieves the image (determined to be substantially similar to the detected image) from table T1, and controls display 32 so as so present the retrieved image on the display 32. It should be noted that this step may also be performed so as to present other appropriate information on the display 32, such as the detected image, the name of the cancer cell corresponding to the image, and the names of the cancer cells, proteins, and/or markers corresponding to these images. Appropriate scaling factors may also be employed during these procedures.

These procedures for determining the shape and/or size of the cancer cells are preferably performed before block M, where the system resolution and magnification level are increased, so that the objective 16 provides a 1:1 magnification level, although in other embodiments, other magnification levels may be employed. In these embodiments, the other magnification levels are taken into account in determining the area and shape of the cancer cells (i.e., appropriate scaling factors are employed).

Figure 12:
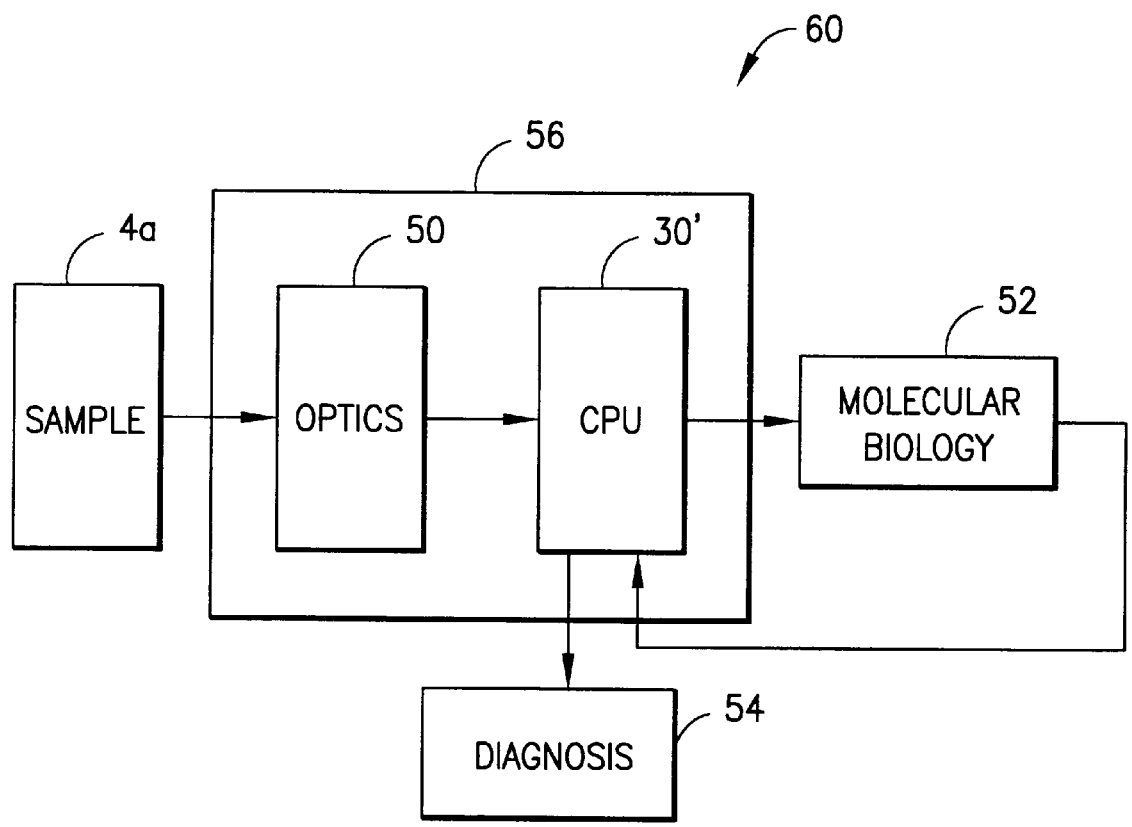

Reference is now made to FIG. 12 which shows an exemplary block diagram 60 that includes the sample 4a, a molecular biology block 52, a diagnosis block 54, and the imaging system of the invention (labelled "56"), including the CPU 30' and a block 50 representing the various optical components 3–25c of the imaging system of the invention. In view of the above description of the invention, it can be appreciated that the imaging system enables the sample 4a to be examined for the presence of cancer-related proteins, using multiple markers in the sample 4a. This is accomplished using the initial screening mode procedures described above. After it is determined that one or more cancer-related proteins are included in the sample 4a, procedures in accordance with the spectral and temporal analyses of the invention may be performed within CPU 30' in order to identify the particular types of proteins that are included in the sample 4a. It should be noted that the system of FIG. 12 may be embodied as a trainable neural network-based system which employs artificial intelligence techniques for enabling these and other determinations to be made regarding the sample 4a. By example, based the type(s) of protein(s) identified during the temporal/spectral analysis of the invention, it can be determined (at block 52) which type(s) of cancerous cells produced the protein(s) in the manner described above, and it also can be determined whether or not a particular gene within DNA of the cell tissue (from sample 4a) that produced the protein(s) is defective or deviant, using appropriate molecular biology techniques. A diagnosis/recommendation may then be made by medical personnel at block 54. By example, assuming that one or more genes were determined to be defective, it may be appropriate to replace these genes with suitable chemical substitutes. Being that particular types of cancerous cells can be identified based on an identification of proteins included in the sample 4a, the imaging system of the invention enables cancer to be detected early in its course of development. By example, the identification of proteins in the sample 4a can indicate break points in a human chromosome, enabling further procedures to be performed for simultaneously mapping all of the twenty two human chromosomes, thereby enabling the human genome program to be accelerated.

While the invention has been particularly shown and described with respect to preferred embodiments thereof, it will be understood by those skilled in the art that changes in form and details may be made therein without departing from the scope and spirit of the invention. By example, in another embodiment of the invention, a prism 23 may be employed in the imaging system of the invention in lieu of the grating 20. Also, although the method of the invention has been described in the context of employing imaging system 1' (of FIGS. 1b and 1c) for examining the sample 4a, it should be noted that in suitable cases, the imaging system 1 of FIGS. 1a and 1b may be employed. In this case, the system 1 may be employed to illuminate the sample 4a with only a single wavelength at a time (i.e., for each "step") in order to enable the sample 4a to be examined for the presence of proteins. Where the imaging system 1 is employed, the method of the invention is performed in a similar manner as was described above, except that the sample 4a is illuminated with only a single wavelength for each "step". Also, the durations of the various time periods (e.g., the first and second predetermined time periods) described above, as well as the dimensions (e.g., width (W), (W1), and (W2), and length (L), etc.) described above for the various components of the imaging system of the invention, are intended to be exemplary in nature and not limiting to the invention. Also, the steps of advancing the sample slide 4 may be performed at any suitable frequency, as controlled by the CPU 30 or by an operator of the CPU 30.

Furthermore, although as was previously described the preferred duration of the pulses fired from the source illuminator 3 is approximately Ins, other pulse durations may also be employed, depending on applicable performance criteria. By example, the selected pulse duration may depend on 1) the selected rate at which the sample slide 4 is advanced 2) a selected rate at which excitation wavelengths are varied, and/or 3) anticipated marker emission excitation response times. The pulse rate of the source illuminator 3 may also be selected with these considerations in mind.

Moreover, although the invention is described in the context of the sample slide 4 being advanced for each step by a distance that is substantially equal to the width (W1) of each individual slit of the mask 14, it should be noted that the stage 18 may be controlled so as to displace the slide 4 by other suitable distances. By example, assuming that the magnification level of objective 16 is increased at block M so as to cause the individual slit images from slit image groups 14a"–14c" to illuminate a greater area of the sample 4a, wherein each individual slit image has a greater width than that described above, then the steps of advancing the slide 4 may be performed by displacing the slide 4 by a distance that is equivalent to this greater width. Furthermore, it should be noted that although the spectral and temporal analyses are described in the context of there being four pulse firings from the source illuminator 3 for each step, it is also within the scope of this invention for there to be more or less than this number of pulse firings, depending on, for example, the fluorescent response decay time periods of the markers employed in the sample 4a.

It should be further noted that the imaging systems 1 and 1' of the invention preferably have a capability of simultaneously evaluating wavelengths detected by the detector array 25 at a rate of approximately 1000 pixels (detector array elements) per second for the scan direction, and at a rate of approximately 256,000 pixels per second for the cross-scan direction. Moreover, the imaging systems 1 and 1' of the invention are not limited to detecting and identifying only cancer-related proteins. These systems 1 and 1' may also be employed for detecting other desired types of substances and/or cells.

Furthermore, it should be noted that invention is not limited for use only with a slide 4. By, example, an opaque substrate may be employed in lieu of the slide 4. Also, assuming that a transparent substrate is employed, it is within the scope of this invention to excite the fluorescent materials through this transparent substrate. By example, the excitation wavelengths may be provided from a location underneath the transparent slide for exciting the fluorescent markers.

What is claimed is:

1. An imaging system for detecting the presence of organic substances in a sample, at least certain types of the organic substances being bound with specific types of fluorescent materials, the imaging system comprising:

a tunable excitation source for illuminating at least a portion of the sample with at least one excitation wavelength for causing one or more of the fluorescent materials to emit their respective characteristic wavelengths;

a photodetector array disposed for detecting the emitted characteristic wavelengths, said photodetector array being responsive to detecting said emitted characteristic wavelengths for outputting signals corresponding to detected ones of the emitted characteristic wavelengths;

an output-user interface; and processing means coupled to an output of said photodetector array and to said output-user interface, said processing means being responsive to receiving at least one of said signals output by said photodetector array for controlling said output-user interface to generate a user-perceptible indicator indicating that at least one of said organic substances is present within the sample.

2. An imaging system as set forth in claim 1, wherein the organic substances include various types of proteins associated with corresponding types of cancer cells.

3. An imaging system as set forth in claim 1, wherein said imaging system further comprises:

a data table, said data table being bidirectionally coupled to said processing means, said data table storing a plurality of reference wavelength values and information identifying the organic substances, each of the reference wavelength values corresponding to at least a respective one of the organic substances;

storage means, said storage means being bidirectionally coupled to said processing means and including a plurality of groups of storage bins, each of said groups of storage bins corresponding to at least one of the reference wavelength values stored in said data table;

wherein said processing means is also responsive to receiving said signals output by said photodetector array for storing individual ones of these signals in corresponding ones of the storage bins, and wherein said processing means also correlates individual ones of said groups that include said corresponding ones of said storage bins to corresponding ones of the reference wavelength values and to corresponding ones of the organic substances identified by the information stored in the data table, said processing means also for controlling the output user-interface for presenting to a user a message identifying the corresponding ones of the organic substances as being present in the sample.

4. An imaging system as set forth in claim 1, and further comprising:

a data table, said data table being bidirectionally coupled to said processing means, said data table storing a plurality of reference wavelength values and information identifying the organic substances, each of the reference wavelength values being associated with at least one of the organic substances, said data table also storing reference decay time constant values, each of the reference decay time constant values corresponding to a respective one of the reference wavelength values and to a respective one of the organic substances; and storage means, said storage means being bidirectionally coupled to said processing means and including a plurality of groups of storage bins, each of the groups of storage bins corresponding to at least one of the reference wavelength values stored in said data table;

wherein said processing means is also responsive to receiving said signals output by said photodetector array for storing individual ones of these signals in corresponding ones of the storage bins, said processing means also for calculating respective emission decay time constant values based on respective ones of the signals stored in the storage bins, said processing means also for determining whether individual ones of the groups of storage bins having signals stored therein correspond to respective ones of said reference wavelength values which are associated with more than one of the organic substances, wherein said processing means is responsive to determining that individual ones of these groups of storage bins correspond to respective ones of these reference wavelength values for correlating the calculated emission decay time constant values to corresponding ones of the reference decay time constant values and to corresponding ones of the organic substances, and wherein said processing means is also for controlling the output user-interface for presenting to a user a message identifying the corresponding ones of the organic substances as being present in the sample.

5. An imaging system as set forth in claim 1, wherein said tunable excitation source includes a source illuminator for generating a pulsed beam that includes a plurality of wavelengths, the plurality of wavelengths including the at least one excitation wavelength, and wherein said imaging system further comprises:

first means disposed for receiving said pulsed beam from said source illuminator, said first means for selecting the at least one excitation wavelength for being output from said first means as a resultant beam;

second means disposed for receiving the resultant beam output by said first means, said second means for converting the resultant beam to multiple image beams; and a first focussing optic for focussing the multiple image beams to said portion of said sample to illuminate said portion of said sample.

6. An imaging system as set forth in claim 5, wherein said first focussing optic includes an objective.

7. An imaging system as set forth in claim 5, wherein said first means includes:

a slit optic;

a second focussing optic;

a grating; and a collimating lens disposed between said grating and said source illuminator for receiving said pulsed beam from said source illuminator and for collimating said pulsed beam to provide a resultant, collimated pulsed beam to said grating;

wherein said grating diffracts said resultant, collimated pulsed beam to provide a beam portion to said second focussing optic, wherein said second focussing optic collimates said beam portion and provides a further beam portion to said slit optic, said further beam portion including a band of wavelengths that includes the at least one excitation wavelength, and wherein said slit optic is responsive to receiving said further beam portion for selecting the at least one excitation wavelength for being output from said slit optic as said resultant beam.

8. An imaging system as set forth in claim 5, wherein said first means includes:

a slit optic;

a second focussing optic;

a mirror; and a collimating lens disposed between said mirror and said source illuminator for receiving said pulsed beam from said source illuminator and for collimating said pulsed beam to provide a resultant, collimated pulse beam to said mirror;

wherein said mirror reflects said resultant, collimated pulsed beam to said second focussing optic as a beam portion, wherein said second focussing optic collimates said beam portion and provides a further beam portion to said slit optic, said further beam portion including a band of wavelengths that includes the at least one excitation wavelength, and wherein said slit optic is responsive to receiving said further beam portion for selecting the at least one excitation wavelength for being output from said slit optic as said resultant beam.

9. An imaging system as set forth in claim 5, wherein said second means includes:

an optical mask, the optical mask including a plurality of rows of slits, wherein adjacent ones of the rows of slits are separated from one another by predetermined distances, and wherein the slits of individual ones of the plurality of rows are horizontally offset from the slits of other ones of the plurality of rows;

a cylindrical lens disposed for receiving the resultant beam output by said first means, said cylindrical lens for outputting a further beam in response to receiving said resultant beam;

a lenslet array disposed between said cylindrical lens and said optical mask, said lenslet array comprising a plurality of lenslets, said lenslet array for receiving said further beam from said cylindrical lens, wherein the further beam received by the lenslet array illuminates said plurality of lenslets, and wherein in response to said lenslet array being illuminated by said further beam, individual ones of said lenslets focus a respective portion of said further beam to a respective one of the plurality of rows of slits of said optical mask; and wherein in response to receiving respective portions of said further beam from said lenslets, respective ones of said plurality of rows of slits transmit a respective plurality of the multiple image beams to said first focussing optic, and wherein in response to receiving respective pluralities of the multiple image beams, said first focussing optic focusses respective ones of these pluralities of multiple image beams to respective portions of said sample.

10. An imaging system as set forth in claim 1, wherein said photodetector array includes a radiation sensitive surface having a plurality of rows of radiation detection elements, and wherein said imaging system further comprises means for directing those ones of said emitted characteristic wavelengths that are within predetermined wavelength bands to particular ones of said rows of radiation detection elements which correspond to these predetermined wavelength bands.

11. An imaging system as set forth in claim 10, wherein said characteristic wavelengths emitted by said fluorescent materials are part of radiation beams emitted by said fluorescent materials, and wherein said directing means further comprises:

a collimating lens;

a diffraction device;

a second focussing optic;

a slit optic, the slit optic including a plurality of rows of slits, wherein adjacent ones of the rows of slits are separated from one another by predetermined distances, and wherein the slits of individual ones of the plurality of rows are horizontally offset from the slits of other ones of the plurality of rows;

splitting means disposed for receiving said radiation beams, said splitting means for splitting said radiation beams to provide resultant beam portions, said splitting means also for focussing said resultant beam portions to said slit optic;

wherein in response to said slit optic receiving said resultant beam portions, said rows of slits transmit corresponding beams to said collimating lens, said collimating lens being responsive to receiving said corresponding beams from said slit optic for collimating said corresponding beams to provide a collimated beam to said diffraction device, wherein said diffraction device is responsive to receiving said collimated beam for separating wavelengths included in said collimated beam into corresponding ones of said predetermined wavelength bands, said diffraction device also for providing a diffracted beam that includes separated ones of said wavelengths to said second focussing optic, said separated wavelengths including said emitted characteristic wavelengths, and wherein said second focussing optic is responsive to receiving said diffracted beam for directing said emitted characteristic wavelengths to said rows of radiation detection elements.

12. An imaging system as set forth in claim 11, wherein said diffraction device includes a prism.

13. An imaging system as set forth in claim 11, wherein said diffraction device includes a grating.

14. An imaging system as set forth in claim 1, wherein said processing means is responsive to receiving said signals output by said photodetector array for detecting amplitudes of said signals, said processing means also determining whether at least one of the detected amplitudes exceeds a predetermined threshold level, wherein said processing means is responsive to determining that at least one of said amplitudes exceeds said predetermined threshold level for controlling said output user-interface for generating said user-perceptible indicator.

15. An imaging system for detecting the presence of organic substances in a sample, at least certain types of the organic substances being bound with specific types of fluorescent materials, the imaging system comprising:

an output user-interface;

a tunable excitation source for illuminating at least a portion of said sample with at least one excitation wavelength for causing one or more of the fluorescent materials to emit their respective characteristic wavelengths;

means for spatially dispersing the emitted characteristic wavelengths as a function of wavelength;

a photodetector array disposed for simultaneously detecting dispersed ones of the emitted characteristic wavelengths, and for outputting signals corresponding to detected ones of these dispersed emitted characteristic wavelengths; and processing means coupled to an output of said photodetector array and to said output user-interface, said processing means being responsive to receiving at least one of said signals output by said photodetector array for controlling said output user-interface for generating an indicator indicating that at least one of said organic substances is present within the sample.

* * * * *